United States Patent [19]
Ghoshal et al.

[11] Patent Number: 5,986,094
[45] Date of Patent: *Nov. 16, 1999

[54] 4'-METHYL SUBSTITUTED FLUORESCEIN DERIVATIVES

[75] Inventors: Mitali Ghoshal, Neshanic Station; Salvatore Joseph Salamone, Stockton; Robert Sundoro Wu, West Orange, all of N.J.

[73] Assignee: Roche Diagnostics Corporation, Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/844,488

[22] Filed: Apr. 18, 1997

Related U.S. Application Data

[60] Provisional application No. 60/016,281, Apr. 24, 1996.
[51] Int. Cl.$^6$ ...................... C07D 493/10; C07D 405/14
[52] U.S. Cl. .......................... 544/230; 540/543; 546/15; 549/223
[58] Field of Search ................ 544/230; 546/15; 540/543

[56] References Cited

U.S. PATENT DOCUMENTS

| | | | |
|---|---|---|---|
| 4,329,461 | 5/1982 | Khanna et al. | 544/375 |
| 4,510,251 | 4/1985 | Kirkemo et al. | 544/300 |
| 4,614,823 | 9/1986 | Kirkemo et al. | 544/300 |
| 5,340,750 | 8/1994 | Adamczyk et al. | 436/537 |

FOREIGN PATENT DOCUMENTS

| | | |
|---|---|---|
| 0 110 186 | 11/1983 | European Pat. Off. . |
| 0201751 | 11/1986 | European Pat. Off. . |
| 0 232 736 | 1/1987 | European Pat. Off. . |
| 0218010 | 4/1987 | European Pat. Off. . |
| 0 252 404 | 6/1987 | European Pat. Off. . |
| 0 297 303 | 6/1988 | European Pat. Off. . |
| 0 373 508 | 12/1989 | European Pat. Off. . |
| 0457213 | 11/1991 | European Pat. Off. . |
| 2518096 | 6/1983 | France . |
| 2081257 | 2/1982 | United Kingdom . |
| 2111476 | 7/1983 | United Kingdom . |

OTHER PUBLICATIONS

Chemical Abstracts, vol. 107, p. 81, No. 70919h (1987), Shipchandler et al.

Dandiker, et al.; Biochem. Biophys. Res. Comm.; 5:299 (1961).

D. Colbert, et al., "Single–Reagent Polarization Fluoroimmunoassay for Barbiturates in Urine," Clinical Chemistry, vol. 30, No. 11, 1984, pp. 1765–1769.

M. Ghoshal, et al., *Novel 4'–Hydroxymethyl fluorescein: Synthesis and Use in Fluorescence Polarization Immunoassay*, Aug. 1996, Abstract for 212th ACS National Meeting, Orlando, Florida.

Shirchandler et al., "4'–[Aminomethyl]Fluorescein and its N–alkyl Derivatives: Useful Reagents in Immunodiagnostic Techniques," Analytical Biochemistry, 1987, pp. 89–101.

A. Sidki, et al., "Direct Determination of Phenobarbital in Serum or Plasma by Polarization Fluoroimmunoassay," Therapeutic Drug Monitoring, vol. 4, No. 4, 1982, pp. 397–403.

A. Soto, et al., "Radial Partition Immunoassay for Quinidine: Synthesis of Immunogen and Label," Clinical Chemistry, vol. 29, No. 6, 1983, pp. 1200–1201.

*Primary Examiner*—Emily Bernhardt
*Attorney, Agent, or Firm*—Marilyn L. Amick; Roche Diagnostics Corporation

[57] ABSTRACT

The present invention relates to a novel class of tracer compounds for fluorescence polarization imunoassays. The novel 4'-methyl fluorescein derivatives are conjugated to ligands via cyclic linkers.

2 Claims, 9 Drawing Sheets

4'-METHYL SUBSTITUTED FLUORESCEIN DERIVATIVES

This is application claims priority under 35 USC §119(e), the provisional application Serial No. 60/016,281, filed Apr. 24, 1996.

BACKGROUND OF THE INVENTION

The present invention relates generally to methods and reagents used for the determination of ligands in biological fluids. In particular, the present invention relates to a novel class of 4'-methyl substituted fluorescein conjugates useful as tracer reagents in fluorescence polarization immunoassays.

Drug levels in serum samples can be determined through competitive binding immunoassays. Competitive binding immunoassays for measuring the concentration of an analyte (also referred to as a ligand), such as a drug in a test sample are based on the competition between a ligand in a test sample and a labeled reagent, referred to as a tracer, for a limited number of receptor binding sites on antibodies specific to the ligand and tracer. The concentration of ligand in the sample determines the amount of the tracer that will specifically bind to an antibody. The amount of tracer-antibody conjugate produced can be quantitatively measured and is inversely proportional to the quantity of ligand in the test sample.

Examples of ligands or drugs measurable by the methods of the present invention include steroids such as estriol, adrenocorticotropic hormone (ACTH), estrone, cholesterol, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triodothyroxine, histamine, serotonin, prostaglandins such as prostaglandin E(PGE), prostaglandin F(PGF), prostaglandin A(PGA); anti-asthamatic drugs such as theophylline; antineoplastic drugs such as doxorubicin and methotrexate; antiarrhythymic drugs such as disopyramide, lidocaine, procainamide, propranolol, quinidine, N-acetyl procainamide; anticonvulsant drugs such as phenobarbital, phenytoin, primidone, valporoic acid, carbamazepine, flecainide and ethosuximide; antibiotics such as penicillins, cephalosporins, erythromycin, vancomycin, gentamicin, amikacin, chloramphenicol, streptomycin and tobramycin; antiarthritic drugs such as salicylates; antidepressant drugs including tricyclics such as nortriptyline, amitriptyline, imipramine and desipramine; and the like as well as the metabolites thereof. In addition, drugs may include drugs of abuse such as morphine, heroin, hydromophone, oxymorphone, methadone, codeine, hydrocodone, dihydrocodeine, dihydrohydroxy codeinone, dextromethorphan, phenazocine, benzoyl ecgonine, tetrahydro-cannabinoids (THC), barbiturates, benzodiazepine, lysergic acid diethylamide (LSD), propoxyphene, phencyclidine, amphetamines, methaqualone, and their metabolites may be measured in accordance with the methods of the present invention. In addition, environmental pollutants may be measured in accordance with the methods of the present invention. Examples of environmental pollutants include pesticides, herbicides, insecticides, fungicides such as polychlorinated biphenyls (PCBs), atrazine, simazine, terbutryn, s-triazines, amitrole, trifluralin, nortflurazon, permethrin, cypermethrin, paraquat, alachlor, metolachlor, chlorsulfuron, phenylurea herbicides, aldrin, chlordane, endosulan, parathion, dioxins, 2-aminobenzimidazole, pentachlorophenol, benzo-α-pyrene, polyaromatic hydrocarbons (PAHs) and their metabolites.

Fluorescence polarization (FP) is well known in the immunoassay field as providing a quantitative means for measuring the amount of tracer-antibody conjugate produced in a competitive binding immunoassay (see *Biochem. .Biophys.Res.Comm.* 5:299, 1961). In general, fluorescent polarization techniques are based on the principle that a fluorescein labeled compound when excited by linearly polarized light will emit fluorescence having a degree of polarization inversely related to its rate of rotation.

In fluorescence polarization immunoassays (FPIA), fluorescence polarization is a reproducible function of the ligand or drug concentration, and thus is suitable for the quantitative determination of ligand or drug concentrations in serum for the purpose of therapeutic drug monitoring. When tracer, serum containing antibodies specific for the drug to be measured, and drug-free patient serum are mixed together, most of the tracer binds to the antibodies. As a result, when the bound tracer is excited with polarized light at 489 nm, the light emitted at 520 nm remains highly polarized. However, if drug is present in the patient sample, the drug will compete with the tracer for binding to the antibodies. Thus, more of the tracer will remain unbound and the emitted light is depolarized.

An FPIA according to the present invention can be any type of automated or manual FPIA. Preferably the FPIA is carried out on the automated COBAS FARA II® chemistry system (Roche Diagnostic Systems, Inc., Branchburg, N.J.) which can measure the binding of fluorescein labeled drug (the tracer) to specific antibodies (see Dandliker and Feigen, *Biochem. Biophys. Res. Comm.* 5:299, 1961).

In FPIA, the results can be quantified in terms of millipolarization units (mP) from which a calibration curve can be determined and the span can be calculated. The span is the difference (or delta) between the maximum and minimum binding as measured in mP units (delta mP) of the tracer to the antibody as the free drug competes with the bound tracer for antibody binding sites. A larger span provides for better precision in FPIA. The polarization of fluorescence decreases in a regular manner as the concentration of the analyte increases. The higher the delta value, or span, the better the precision and sensitivity of the assay. The concentration of drug in the sample can be determined by comparison to a standard calibration curve.

Several fluorescein derivatives from which fluorescein labelled compounds, or tracers, can be prepared are known and are commercially available. The majority of fluorescein derivatives are derived from the 5 or 6 position of fluorescein (also referred to as isomer I for the 5 position and isomer II for the 6 position) and include 5 or 6-N-hydroxysuccinimidylcarboxyfluorescein, 5-aminomethylfluorescein and 5-or 6-dichloro-1,3,5-triazin-2-ylaminofluorescein (DTAF).

Fluorescein derivatives synthesized out of the 4' position of fluorescein are also known. For example, 4'-aminomethylfluorescein is useful as a nucleophile for coupling to drug derivatives or ligands bearing a carboxylic group (see U.S. Pat. No. 4,614,823 and U.S. Pat. No. 4,510,251). The amine group of the fluorescein reacts with a carboxy group of an analyte to form a peptide bond. However, this method does not allow an analyte containing a cyclic ring to be attached directly at the 4'-methyl carbon atom.

Therefore, it is an object of the present invention to provide a fluorescein derivative which can react directly to cyclic amines to provide a cyclic linker between the fluorescein molecule and the analyte.

More particularly, it is an object of the present invention to prepare an improved 4'-methyl substituted fluorescein derivative modified with a linking group which can be readily conjugated to a ligand having a nucleophilic center. It is also an object of the present invention to prepare a 4'-methyl substituted fluorescein derivative which can be readily conjugated to a ligand modified with a linking group having a nucleophilic center.

Further, it is an object of the present invention to prepare a 4'-methyl substituted fluorescein derivative containing a leaving group which can be readily displaced with an amino group, thereby facilitating the linking of the fluorescein to a drug derivative. The 4'-methyl substituted fluorescein itself can be modified with the amino group, preferably by reaction with a cyclic amine. Alternatively, the amino group can be part of a drug derivative to which the 4'-methyl substituted fluorescein can be conjugated, most preferably a drug derivative having a cyclic amine-containing linker.

A further object of the present invention is to provide a 4'-methyl substituted fluorescein derivative which can be used to prepare a fluorescein tracer having a larger dynamic span which leads to a more precise and sensitive performance in the FPIA.

SUMMARY OF THE INVENTION

The present invention relates to a novel class of fluorescein derivatives of the formula

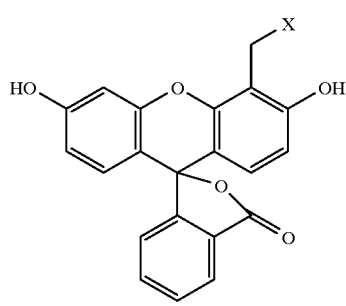

I wherein X is a leaving group selected from the group consisting of hydroxy, halogen, and a sulfonic ester having the formula —O—SO$_2$—R, wherein R is —C$_6$H$_4$—CH$_3$ or CH$_3$.

The fluorescein derivatives of formula I are useful as intermediates in the synthesis of novel reagents which can be used in fluorescence polarization immunoassays.

The present invention also relates to drug-fluorescein conjugates containing a cyclic linker used as tracers in fluorescence polarization immunoassays.

BRIEF DESCRIPTION OF THE FIGURES

The present invention may be more readily understood by reference to the following figures. The numbers used herein following the compounds correlates to the compound numbers shown in FIGS. 1–9.

DETAILED DESCRIPTION OF THE INVENTION

The present invention relates to novel fluorescein derivatives of the formula

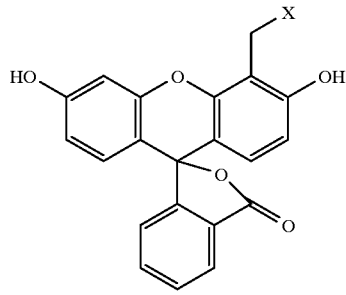

wherein X is a leaving group selected from the group consisting of halogen, hydroxy and a sulphonate ester having the formula —O—SO$_2$—R, wherein R is —C$_6$H$_4$—CH$_3$ or CH$_3$. Preferably X is hydroxy and the fluorescein derivative is 4'-hydroxymethylfluorescein which has the formula

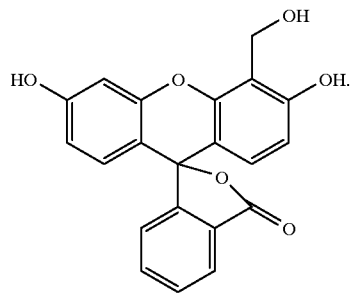

Figure 1:
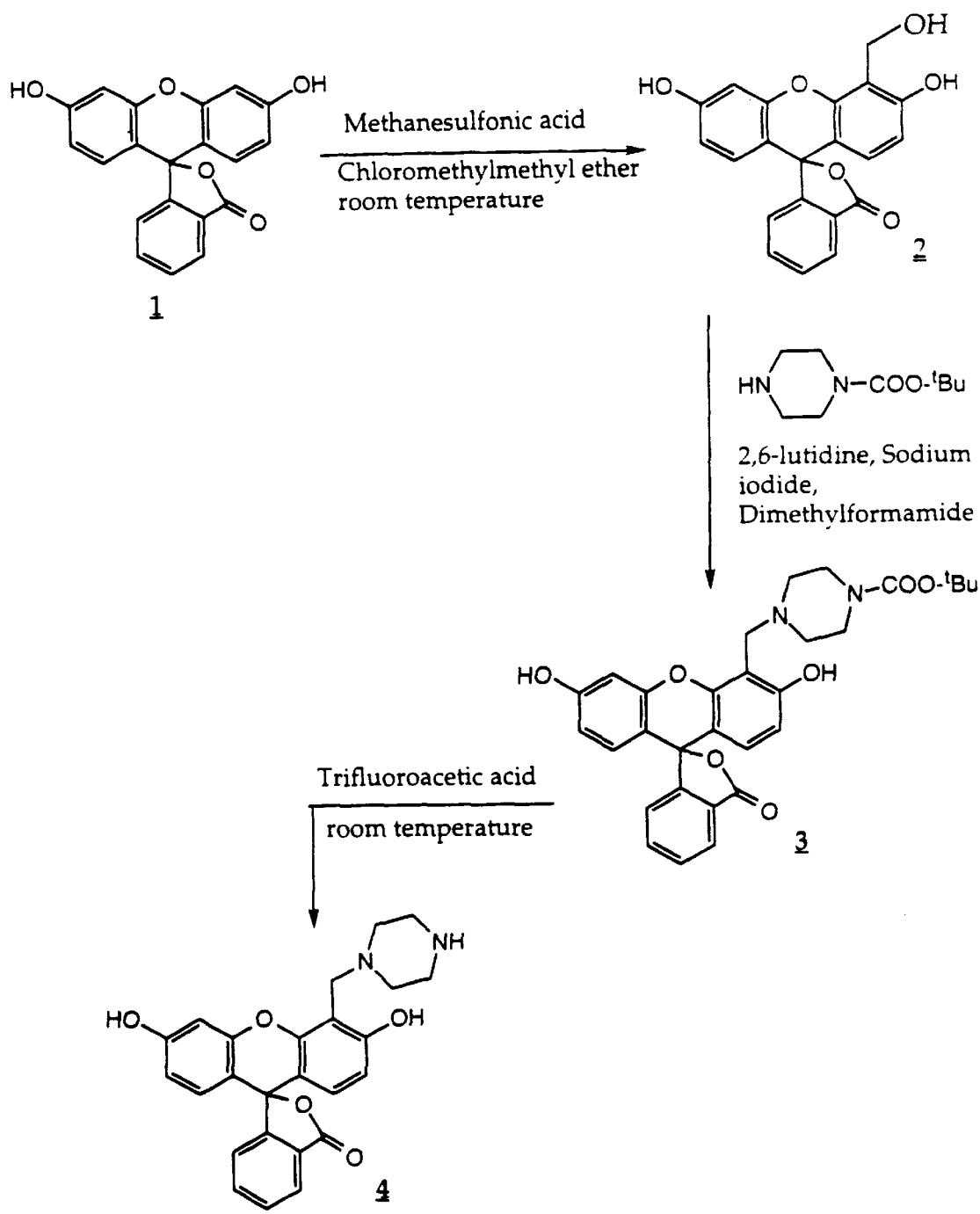
FIG. 1 shows the formulae of the starting materials and intermediates involved in the synthesis of 4'-hydroxymethylfluorescein: [rac-4'-(hydroxymethyl)-3',6'-dihydroxyspiro[isobenzofuran-1(3H),9'-[9H]-xanthen]-3-one] (2) and 4'-piperazinylmethylfluorescein: [rac-3',6'-dihydroxy-4'-(1-piperazinylmethyl)spiro[isobenzofuran-1(3H),9'-[9H] xanthen]-3-one (4).

4'-hydroxymethylfluorescein was obtained via a Friedel-crafts reaction performed on fluorescein using chloromethylmethyl ether in the presence of methanesulphonic acid (FIG. 1).

In one aspect of the present invention, the novel 4'-fluorescein derivatives can be coupled to a cyclic linker to form the novel drug-fluorescein tracers of the present invention.

For example, the 4'-methyl substituted fluorescein derivative was modified to bear a hydroxy leaving group. A nucleophilic reaction was performed on the 4'-fluorescein derivative using a cyclic amine in the presence of an organic base to yield a 4'-methyl substituted fluorescein derivative with a cyclic linker to yield a compound having the formula

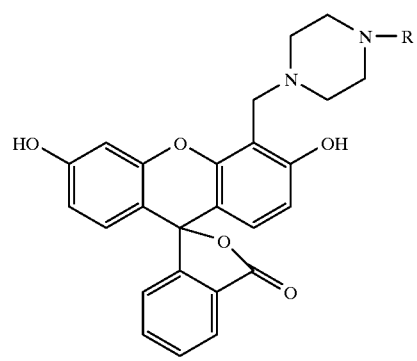

wherein R is selected from H or a drug derivative, for example a valproic acid derivative. This resulting 4'-fluorescein conjugate was then reacted with a drug to yield the novel drug-fluorescein tracers of the present invention.

As is demonstated below, the novel 4'-methyl substituted fluorescein derivatives of the present invention are a useful reagent in the preparation of fluorescein-drug conjugates. It is unusual for a hydroxyl group to be substituted by a nuceophile. Surprisingly, the hydroxy group at the C-4' position can be displaced by a number of nucleophiles, as is described below. The incorporation of a cyclic linker arm at the C-4' methyl group yields a larger span in the fluorescence polarization immunoassays, thus providing a better precision and higher sensitivity. Therefore, tracers containing a cyclic linker arm are superior reagents in the FPIA.

In one embodiment, a nucleophilic reaction was performed on 4'-hydroxymethylfluorescein utilizing t-butyl-1-piperazine carboxylate in the presence of 2,6-lutidine in dimethylformamide (DMF), and sodium iodide at 130–140° C. to yield rac-4-(3',6'-dihydroxy-3-oxospiro-[isobenzofuran-1(3H),9'-[9H]xanthen-4'-yl]methyl)-1-piperazinecarboxylic acid-1,1-dimethylethyl ester (3) (FIG. 1). Deprotection of the t-butyl carbamate (t-Boc) group using trifluoroacetic acid yielded 4'-piperazinylmethylfluorescein (4), having the formula

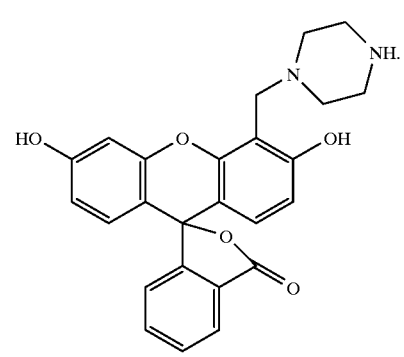

Figure 2:
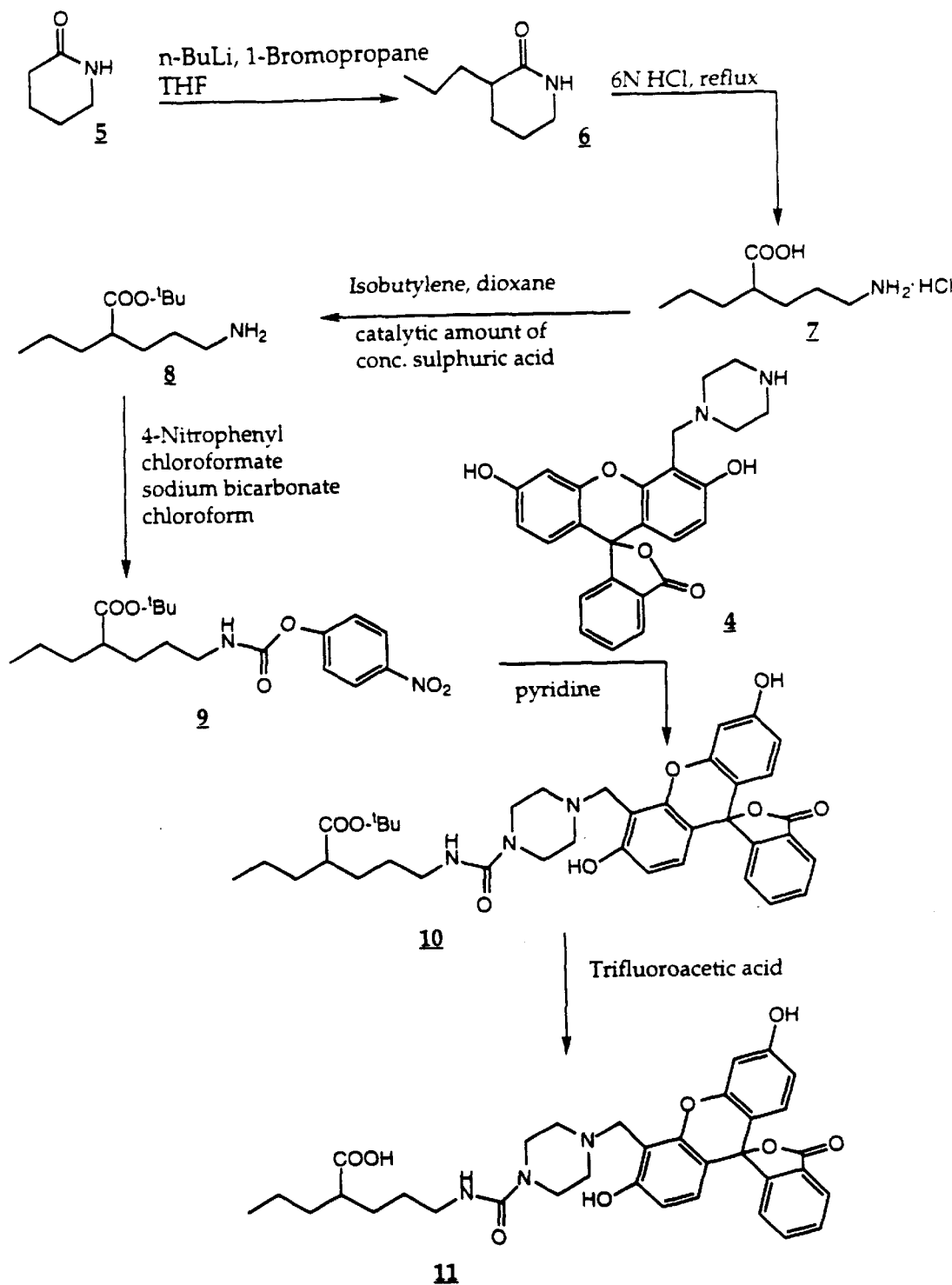
FIG. 2 shows the formulae of the starting materials and intermediates involved in the synthesis of (5-[[[4-[4-[(3',6'-dihydroxy-3-oxospiro-[isobenzofuran-1(3H),9'-[9H] xanthen]-4'-yl)methyl]-1-piperazinyl]-carbonyl]amino]-2-propyl]pentanoic acid (11), a valproic acid FP tracer containing a cyclic linker.

The 4'-piperazinylmethylfluorescein can be conjugated to a ligand or drug to form an FP tracer. For example, 4'-piperazinylmethylfluorescein was used to prepare a valproic acid FP tracer containing a cyclic linker (FIG. 2). The piperazinylmethylfluorescein was coupled to a valproic acid derivative (9) resulting in the formation of the urea (10). Deprotection of the t-Boc group in trifluoroacetic acid yielded the valproic acid tracer containing a cyclic linker, 5-[[[4-[(3',6'-dihydroxy-3-oxospiro[isobenzofuran-1(3H), 9'-[9H]xanthen]-4'-yl)methyl] -1-piperazinyl]carbonyl] amino]-2-propylpentanoic acid (11), having the formula

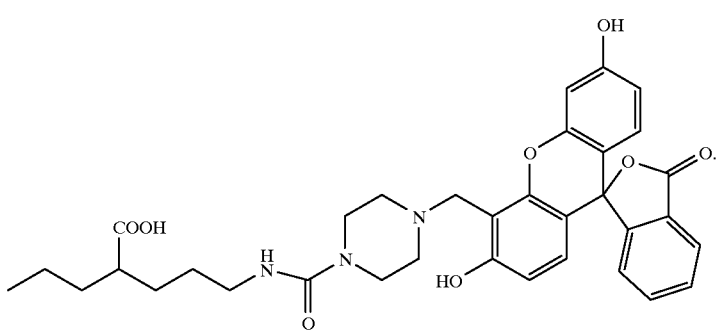

V

Figure 3:
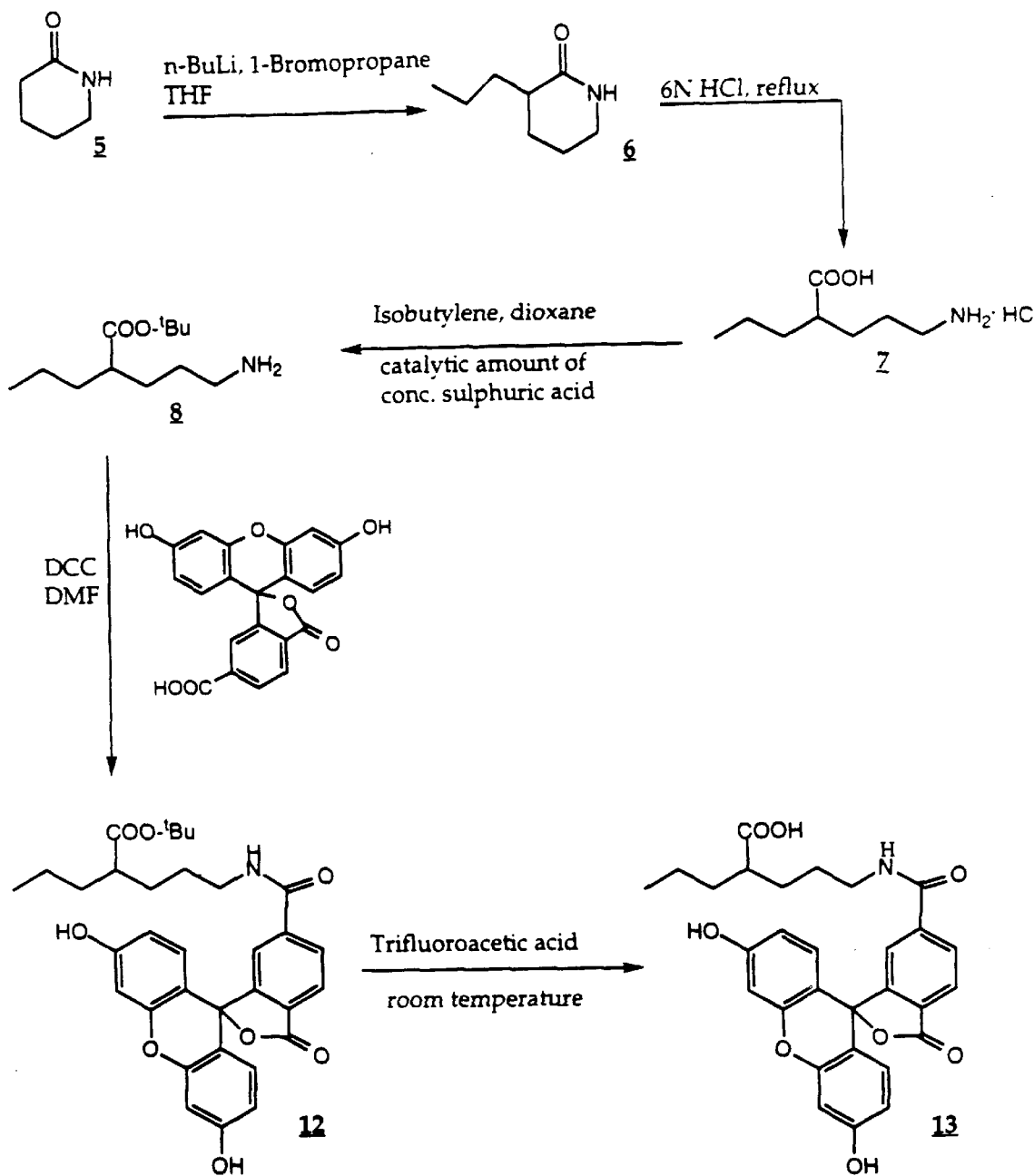
FIG. 3 shows the formulae of the starting materials and intermediates involved in the synthesis of rac-5-[[[3',6'-dihydroxy-3-oxospiro[isobenzofuran-1(3H),9'[9H] xanthen]-6-yl)carbonyl]amino]-2-propylpentanoic acid (13), a valproic acid FP tracer containing an acyclic linker.

The drug-fluorescein conjugate of valproic acid containing an acyclic linker, rac-5-[[[3',6'-dihydroxy-3-oxospiro [isobenzofuran-1(3H),9'[9H] xanthen]-6-yl)carbonyl]amino]-2-propylpentanoic acid (13), was also prepared (FIG. 3). 6-Carboxy N-hydroxysuccinimide ester was coupled with the valproic acid derivative (8) having an amino functionality. Deprotection of the t-Boc group in trifluoroacetic acid provided the valproic tracer without a cyclic linker.

The two valproic acid tracers 5-[[[4-[(3',6'-dihydroxy-3-oxospiro[isobenzofuran-1(3H),9'-[9H] xanthen]-4'-yl)methyl]-1-piperazinyl]carbonyl]amino]-2-propylpentanoic acid (11) and rac-5-[[[3',6'-dihydroxy-3-oxospiro [isobenzofuran-1(3H),9'[9H] xanthen]-6-yl)carbonyl]amino]-2-propylpentanoic acid (13) were evaluated on the COBAS FARA II® chemistry system using polyclonal antisera (COBAS-FP Reagent No. 44065). The span (delta mP) observed in the calibration curve was higher for the tracer containing the cyclic linker (146 mP) when compared to the tracer containing the acyclic linker (121 mP).

The fluorescein derivative reacts directly with cyclic amines to provide a cyclic linker between the fluorescein molecule and the analyte. This type of molecular design retards more freedom of rotation of the drug-flourescein conjugate having the cyclic linker once it is bound to the antibody, providing a greater span than the drug-fluorescein conjugate synthesized in the absence of the cyclic linker. The novel tracer with the cyclic linker demonstrated an improved dynamic range of the standard curve and enhanced polarization when used in the FPIA.

The present invention also relates to a 4'-methyl fluorescein derivative coupled directly to a drug modified with a cyclic linker to produce novel drug-fluorescein conjugates having the general formula

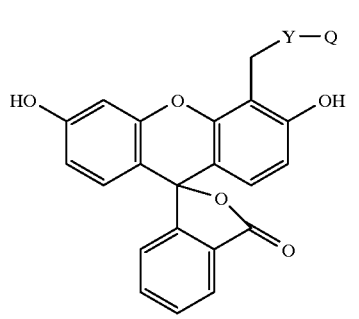

VI wherein Y is a cyclic linker selected from the group consisting of piperazine, homopiperazine, 4-aminomethylpiperidine, 4-carboxypiperidine, proline and 3-carboxydihydropyridine; and Q is a drug, therapeutic agent or environmental pollutant as described herein.

In a preferred embodiment, Y is selected from the group consisting of piperazine, homopiperazine, and 4-aminomethylpiperidine; and Q is a drug selected from the group consisting of thyroxine, acetaminophen, amphetamine, and carbamazapine.

Generally, the process for coupling a 4'-methyl fluorescein derivative, preferably 4'-hydroxymethylfluorescein, to a drug containing a cyclic linker selected from the group consisting of piperazine, homopiperazine or piperidine, comprises reacting 4'-hydroxymethylfluorescein with a drug or ligand containing a cyclic linker in the presence of 2,6 lutidine and sodium iodide in dimethylformamide, at a temperature of from 120° C. to 140° C.

Figure 4:
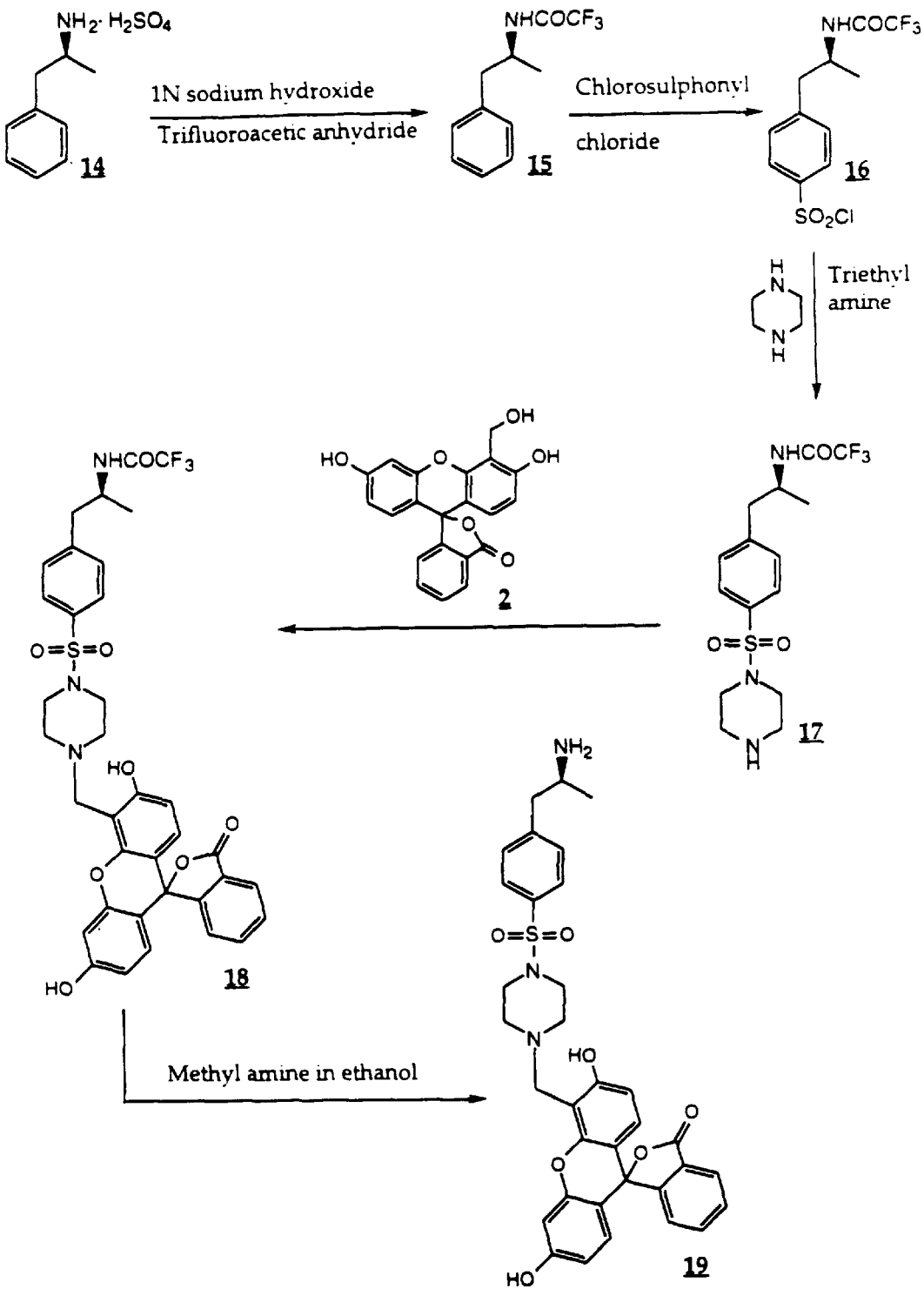
FIG. 4 shows the formulae of the starting materials and the intermediates involved in the synthesis of (S)-4'-[[4-[[4-(2-aminopropyl)-phenyl)phenyl]sulfonyl]-1-piperazinyl]methyl]-3',6'-dihydroxyspiro-[isobenzofuran-1(3H)9'-[9H] xanthen]-3-one (1:1 epimers) (19), an amphetamine FP tracer containing piperazine as a cyclic linker.

An amphetamine FP tracer containing a piperazine linker was synthesized using an amphetamine derivative with a piperazine ring, (S)-2,2,2-trifluoro-N-[1-methyl-2-[4-(1-piperazinyl-sulfonyl)phenyl]ethyl]-acetamide (17), was reacted with 4'-hydroxy-methylfluorescein in the presence of 2,6-lutidine and sodium iodide in dimethylformamide at 120° C. to yield (S)-N-[2-[4-[[4-[(3',6'-dihydroxy-3-oxospiro[isobenzofuran-1(3H),9'-[9H]xanthen]-4'-yl)methyl]-1-pipera-zinyl]sulfonyl]phenyl]-1-methylethyl]-2,2,2-trifluoroacetamide as a 1:1 epimeric mixture (18) (FIG. 4). Upon deprotection by methylamine in ethanol, the amphetamine derivative (S)-4'-[[4-(2-aminopropyl)phenyl]-sulfonyl]-1-piperazinyl]-methyl]-3',6'-dihydroxyspiro [isobenzofuran-1(3H)-9'-[9H]xanthen]-3-one (1:1 epimers) (19) was produced.

Figure 5:
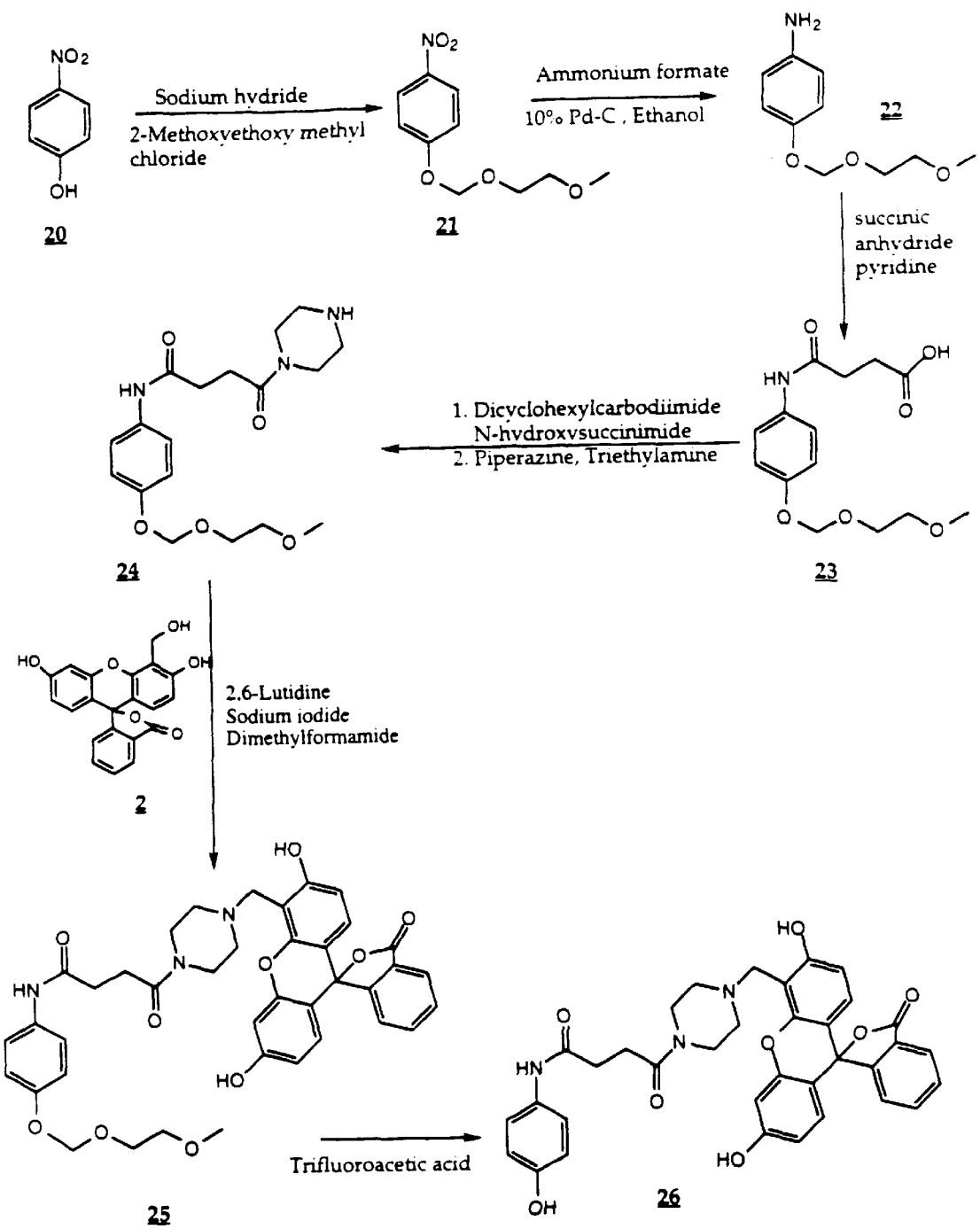
FIG. 5 shows the formulae of the starting materials and the intermediates involved in the synthesis of [rac-4-[(3',6'-dihydroxy-3-oxospiro[isobenzofuran-1(3H),9'-[9H] xanthen]-4'-yl)methyl]-N-(4-hydroxyphenyl)-gamma-oxo-1-piperazinebutamide (26), an acetaminophen FP tracer containing a cyclic linker.

The synthesis of an acetaminophen FP tracer comprising a piperazine linker utilized p-nitrophenol as the starting material which was converted to the methoxyethoxy methyl ether (21) (FIG. 5). The protected nitrophenol was reduced to an amino in the presence of ammonium formate and 10% Pd—C in ethanol to yield 4-[(2-methoxyethoxy)methoxy] benzamine (22). The amino group was succinylated and the resulting acid derivative was coupled to piperazine. The acetaminophen derivative containing the piperazine group was coupled to 4'-hydroxymethylfluorescein followed by deprotection of the methoxyethoxy methyl ether in the presence of trifluoroacetic acid to form rac-4-[(3',6'-dihydroxy-3-oxospiro[isobenzofuran-1(3H),9'-[9H] xanthen]-4'-yl)methyl]-N-(4-hydroxyphenyl)-gamma-oxo-1-piperazinebutamide (26).

Figure 6:
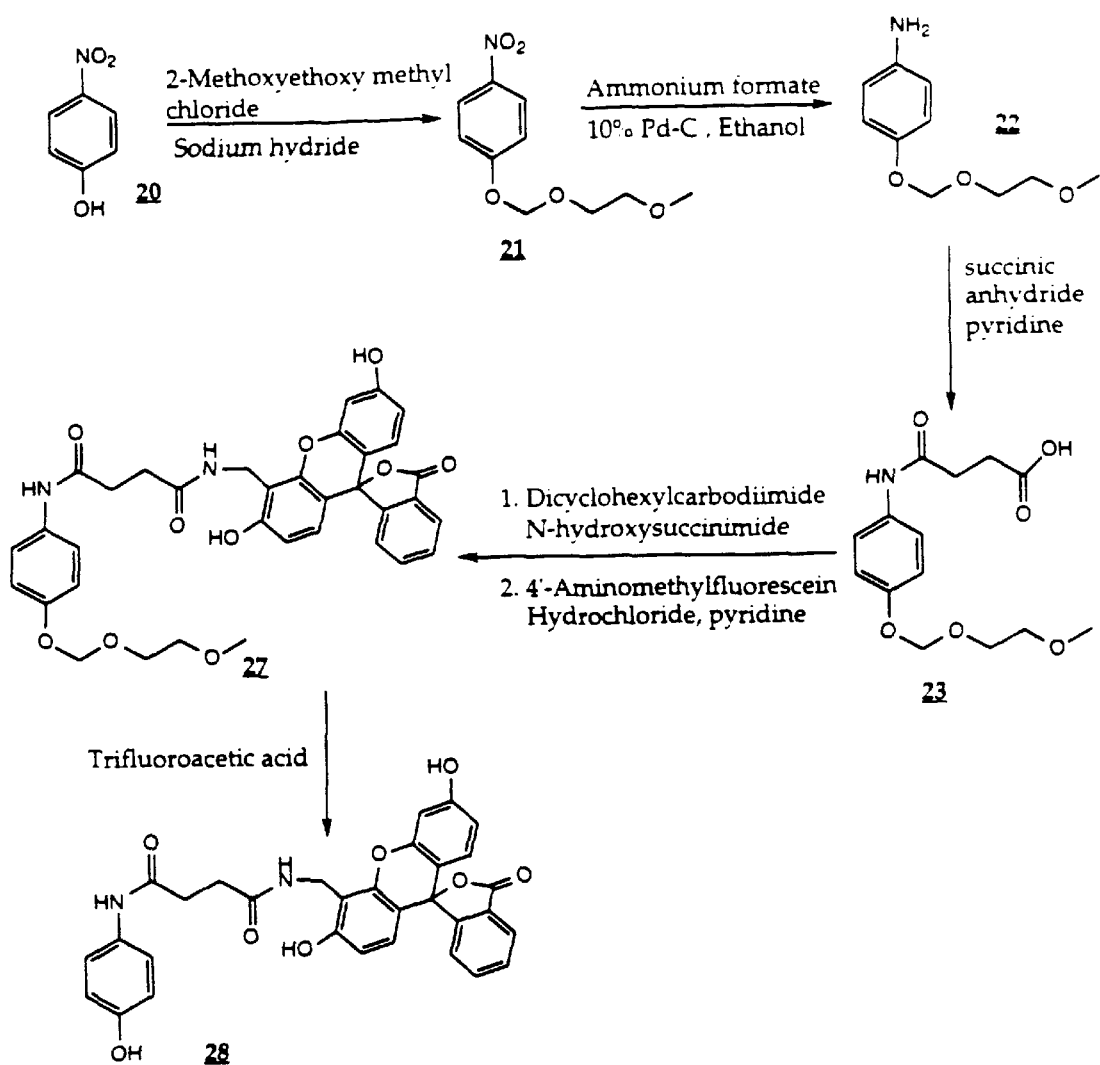
FIG. 6 shows the formulae of the starting materials and the intermediates involved in the synthesis of [rac-4-[3',6'-dihydroxy-3-oxospiro[isobenzofuran-1(3H),9'-[9H] xanthen]-4'-yl)methyl]amino]-N-(4-hydroxyphenyl)-4-oxobutanamide (28), an acetaminophen FP tracer containing an acyclic linker.

For the synthesis of an acetaminophen FP tracer having an acyclic linker, p-Nitrophenol was protected as a methoxyethoxy methyl ether (FIG. 6). The nitro group was reduced to an amino in the presence of ammonium formate and 10% Pd—C in ethanol to yield 4-[(2-methoxyethoxy)methoxy]

benzenamine (22). The amino group was succinylated and the acid derivative produced was coupled to 4'-aminomethylfluorescein. Deprotection of the methoxyethoxy ether (27) in the presence of trifluoroacetic acid yielded rac-4-[[[3',6'-dihydroxy-3-oxospiro-[isobenzofuran-1(3H),9'-[9H] xanthen]-4'-yl)methyl]amino]-N-(4-hydroxyphenyl)-4-oxobutamide (28).

The performance of the two acetaminophen FP tracers was evaluated on the COBAS FARA II® chemistry system using polyclonal antisera (Lot No. P34, Binding Site, California). The results of the comparison of the calibration curves generated by the acetaminophen FP tracers derived out of the 4'-position of fluorescein containing cyclic and acyclic linkers were obtained using an assay protocol such as the one described in Example 31 and are shown in Table 1 below.

TABLE 1

| Calibrator Amount of free acetaminophen | Acetaminophen tracer with cyclic linker 26 mP | Acetaminophen tracer with acyclic linker 28 mP |
|---|---|---|
| 0 µg/mL | 273.9 | 208 |
| 10 µg/mL | 235.4 | 182 |
| 20 µg/mL | 217.6 | 158 |
| 50 µg/mL | 177 | 135 |
| 100 µg/mL | 117.2 | 96 |
| Span (delta mP) | 156.7 | 112 |

As shown in Table 1, the acetaminophen tracer having the cyclic ring, rac-4-[(3',6'-dihydroxy-3-oxospiro [isobenzofuran-1(3H),9'-[9H]xanthen]-4'-yl)methyl]-N-(4-hydroxyphenyl)-gamma-oxo-1-piperazinebutamide (26), had a higher span (156.7 mP), and therefore was more polarized, than the acetaminophen tracer containing the acyclic tracer, rac-4-[[[3',6'-dihydroxy-3-oxospiro [isobenzofuran-1 (3H),9'-[9H]xanthen]-4'-yl) methyl] amino]-N-(4-hydroxyphenyl)-4-oxobutamide (28) (span of 112 mP). This result demonstrated that the tracer having a cyclic linker exhibited a better sensitivity and precision in the FPIA.

Figure 7:
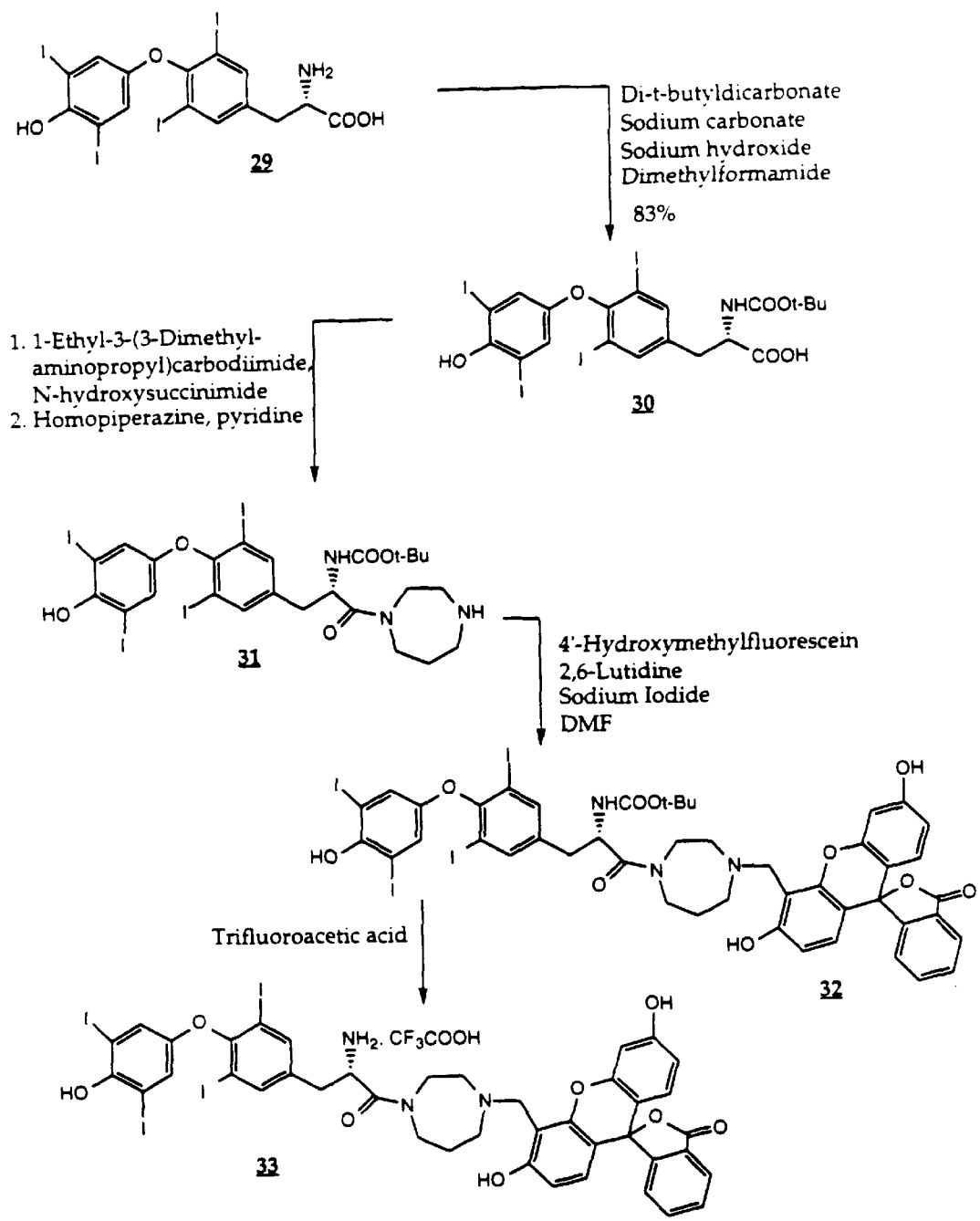
FIG. 7 shows the formulae of the starting materials and the intermediates involved in the synthesis of [(2S)-4'-[[4-[2-amino-3-[4(4-hydroxy-3,5-diiodophenoxy)-3,5-diiodophenyl]-1-oxopropyl]-1-piper-azinyl]methyl]-3',6'-dihydroxyspiro[isobenzofuran-1(3H),9'-[9H]xanthen]-3-one (1:1 epimers) (33), a thyroxine FP tracer containing a cyclic linker.

For the synthesis of a thyroxine FP tracer containing homopiperazine as a linker, thyroxine was treated with di-t-butyl dicarbonate to provide the thyroxine derivative (30) (FIG. 7). The carboxy group of the thyroxine derivative (30) was activated to an N-hydroxysuccinimide ester and coupled to homopiperazine. The thyroxine derivative containing the homopiperazine group (31) was conjugated to 4'-hydroxymethyl fluorescein, followed by deprotection, and yielded (2S)-4'-[4'-[[4-[2-amino-3-[4-(4-hydroxy-3,5-diiodophenoxy)-3,5-diiodophenyl]-1-oxopropyl]-1-piperazinyl]methyl]-3', 6'-dihydroxyspiro-[isobenzofuran-1 (3H)9'-[9H]xanthen]-3-one (1:1 epimers) (33).

The thyroxine tracer was evaluated by FPIA on the COBAS FARA II® chemistry system using a monoclonal antibody (COBAS-FP Reagent No. 46200) and assay protocol similar to that shown in Example 31. Table 2 below provides the data generated for the calibration curve using the novel thyroxine tracer containing a cylic linker.

TABLE 2

| Calibrator Amount of free thyroxine | Thyroxine tracer, 33 mP |
|---|---|
| 0.0 µg/mL | 266.8 |
| 3.0 µg/mL | 254.9 |
| 6.0 µg/mL | 237.9 |

TABLE 2-continued

| Calibrator Amount of free thyroxine | Thyroxine tracer, 33 mP |
|---|---|
| 12 µg/mL | 202.8 |
| 18 µg/mL | 167.1 |
| 24 µg/mL | 133.5 |
| Span (delta mP) | 133.3 |

As shown in Table 2, the fluorescence polarization of the novel thyroxine tracer decreases proportionally as the concentration of the thyroxine calibrator increases, generating a standard dose response curve suitable for the quantitative determination of thyroxine in a sample. Thus, this thyroxine FP tracer is an effective reagent in the FPIA.

Figure 8:
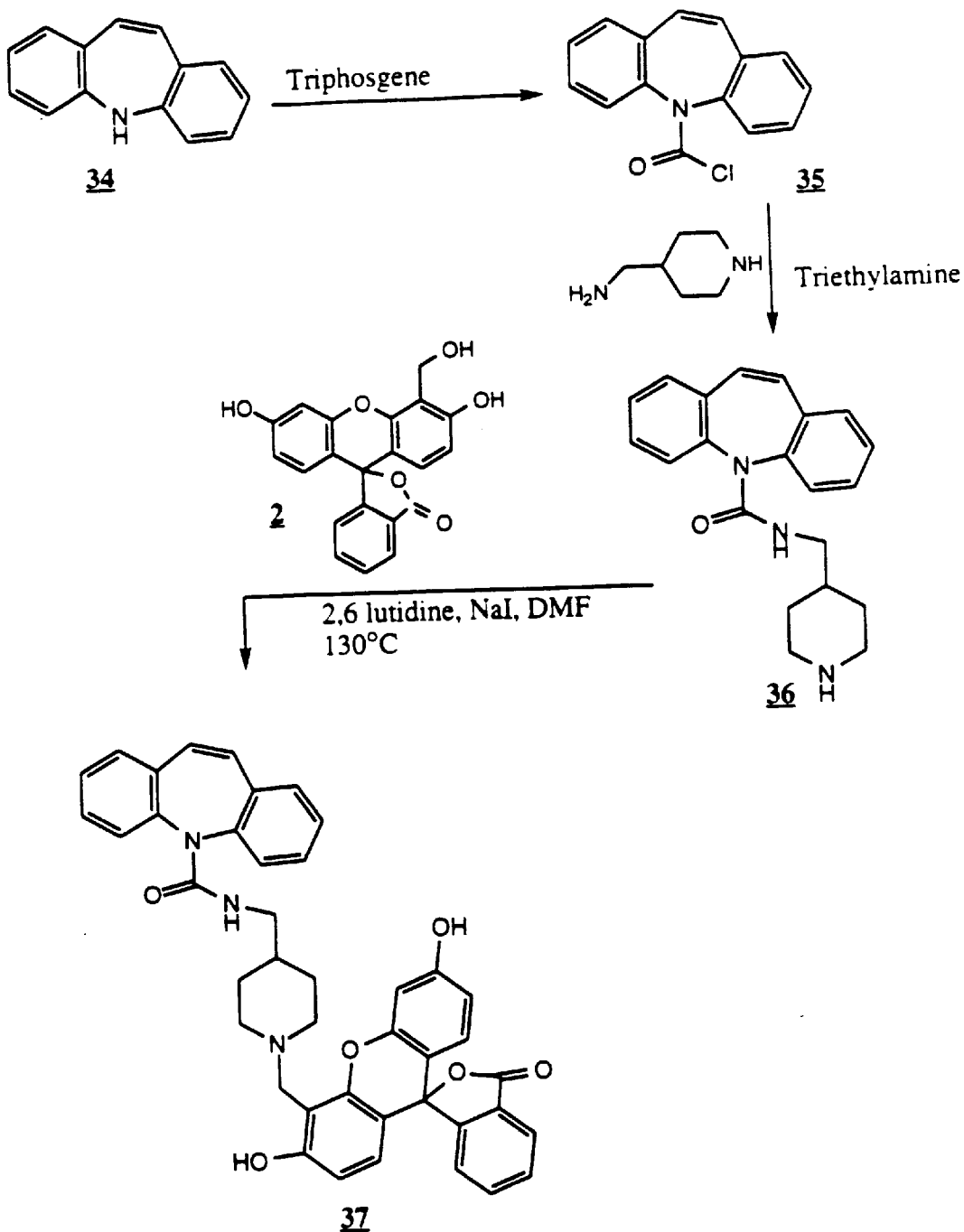
FIG. 8 shows the formulae of the starting materials and the intermediates involved in the synthesis of [N-[[[1-[3',6'-dihydroxy-3-oxospiro[isobenzofuran-1(3H)-9'-[9H]-xanthen]-4'-yl)methyl]-4-piperidinyl]methyl]-5H-dibenzo [b,f]azepine-5-carboxamide (37), a carbamazepine FP tracer containing a cyclic linker.

In the synthesis of a carbamazepine FP tracer containing the cyclic linker piperidine, N-carbamoylchloride (35) was coupled with 4-aminomethylpiperidine to yield a carbamazepine derivative containing a piperidine group (36) (FIG. 8). This carbamazepine derivative was conjugated to 4'-hydroxymethylfluorescein to yield a carbamazepine FP tracer containing a cyclic linker, N-[[1-[(3',6'-di-hydroxy-3-oxospiro-[isobenzofuran-1(3H)-9'-[9H]-xanthen]-4'-yl) methyl]-4-piperidinyl]methyl]-5H-dibenzo[b,f] azepine-5-carboxamide (37).

In addition to the presence of a cyclic linker between fluorescein and the drug molecule, the positioning of the linker arm adjacent to the phenolic ring induces chirality resulting in the hindered rotation of the entire drug-fluorescein, thus improving the dynamic range of the standard curve in the FPIA.

Figure 9:
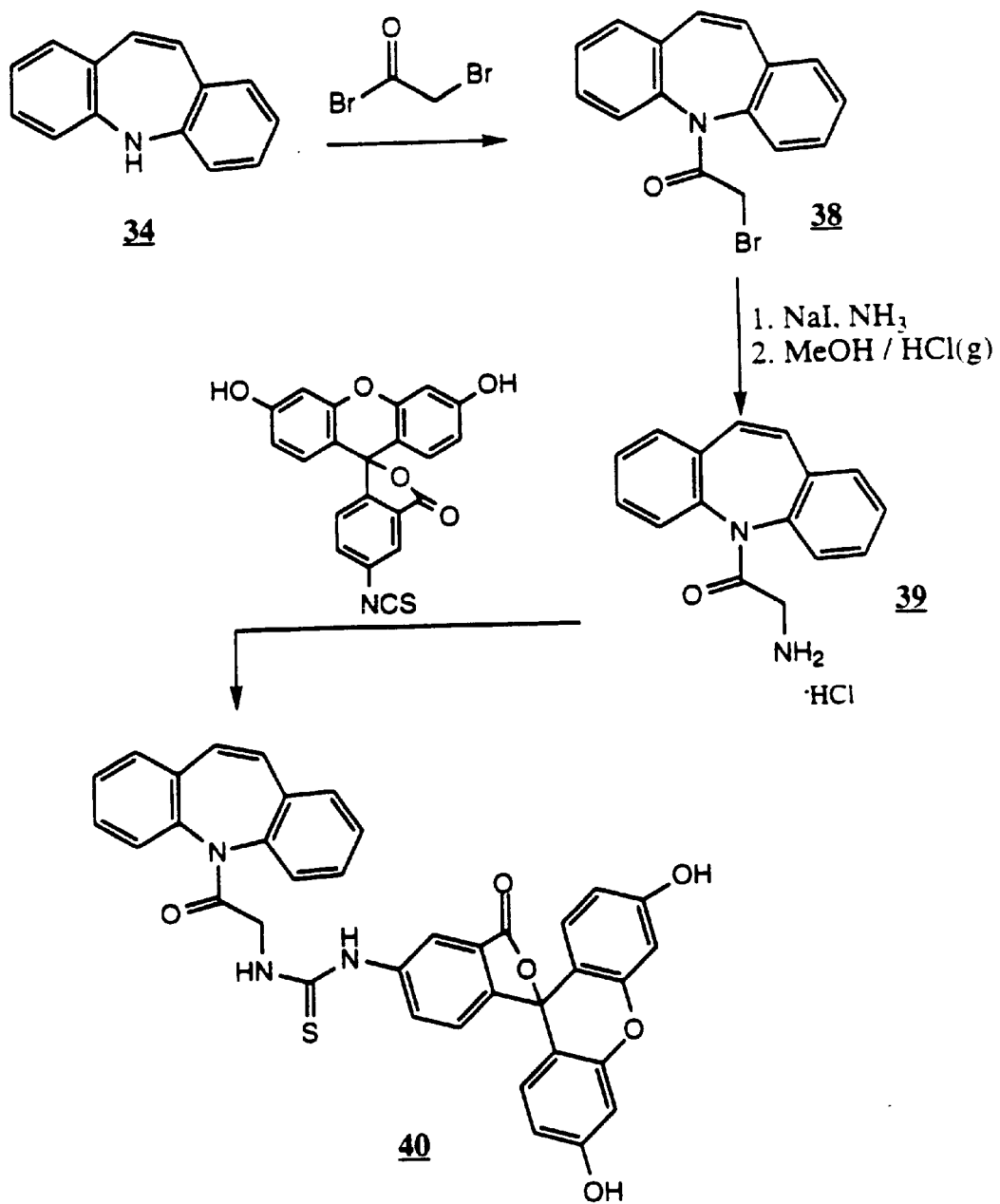
FIG. 9 shows the formulae of the starting materials and the intermediates involved in the synthesis of N-[(5H-dibenz [b,f]azepin-5-ylcarbonyl)methyl]-N-3',6'-dihydroxy-3-oxospiro[isobenzofuran-1(3H,9'-[9H]xanthen-5-yl]thiourea dihydrate(40), a carbamazepine FP tracer containing an acyclic linker.

The preparation of a carbamazepine FP tracer having an acyclic linker is illustrated in FIG. 9. Iminostilbene was reacted with alpha-bromoacetylbromide to provide the bromo derivative (38). The bromo derivative was reacted with ammonia and sodium iodide to yield the amino containing carbamazepine derivative (39). This carbamazepine derivative was coupled to 5-fluoresceinisothiocyanate and yielded the carbamazepine tracer with an acyclic linker N-[(5H-dibenz[b,f]azepin-5-ylcarbonyl)methyl]-N'-3',6'-dihydroxy-3-oxospiro[isobenzofuran-1(3H),9'-[9H] xanthen-5-yl]thiourea dihydrate (40).

The carbamazepine tracers were evaluated by FPIA using an assay protocol similar to the one shown in Example 31 using polyclonal antisera (COBAS-FP Reagent No. 46206). The comparison of the calibration curves generated by the carbamazepine FP tracers containing cyclic and acylic linkers is shown in Table 3.

TABLE 3

| Calibrator, Concentration of free carbamazepine | Carbamazepine tracer with cyclic linker 37 mP | Carbamazepine tracer with acyclic linker 40 mP |
|---|---|---|
| 0 µg/mL | 311.5 | 262.8 |
| 1.25 µg/mL | 292.3 | 241.8 |
| 10 µg/mL | 263.7 | 217.4 |
| 20 µg/mL | 221.6 | 185.8 |
| 50 µg/mL | 183.1 | 151.8 |
| 100 µg/mL | 144.5 | 126.4 |
| Span (delta mP) | 167 | 135.9 |

The data in Table 3 indicates that the presence of a cyclic linker in the carbamazepine tracer (40) substituted out of one of the phenolic rings of fluorescein provides enhanced polarization (span of 167 mP) when compared to the carbamazepine FP tracer containing an acyclic linker arm derived out of the 5-position of fluorescein (span of 135.9 mP), therefore providing higher precision and accuracy in the FPIA.

EXAMPLES

The following are non-limiting examples which illustrate the synthesis of the novel 4'-methyl fluorescein derivatives of the present invention and a fluorescence polarization immunoasassay protocol. The numerical designations of the compounds in the headings and in Examples 1–30 refer to the structural formulae shown in FIGS. 1 through 9.

All solvents were purchased from Fisher Scientific (Springfield, N.J.) unless otherwise stated. Thin layer chromatography using silica gel 60 $F_{254}$ plates and flash grade silica gel for column chromatography were obtained from E.M. Science (Gibbstown, N.J.). 6-Carboxyfluorescein and 4'-aminomethylfluorescein hydrochloride were purchased from Molecular Probes (Eugene, Oreg.). 1-Ethyl-3-(3-dimethylaminopropyl)carbodiimide (EDC), L-thyroxine and d-amphetamine sulfate were purchased from Sigma Chemical Company (St. Louis, Mo.). Ethyl 4-bromobutyrate and di-t-butyl dicarbonate were purchased from Fluka (Switzerland). All other chemicals were purchased from Aldrich Chemical Company (Milwaukee, Wis.).

Example 1

Preparation of rac-4'-(hydroxymethyl)-3',6'-dihydroxyspiro-[isobenzofuran-1(3H),9'-[9H]xanthen]-3-one (2)

To a solution of 50 mg (0.15 mmol) of fluorescein in 0.3 mL of methanesulfonic acid was added 13 µL (0.16 mmol) of chloromethyl methyl ether at room temperature. The mixture was stirred at room temperature for 48 hours. The reaction mixture was poured into 10 mL of ice-cold water. A yellow-orange solid precipitated out and was filtered. The crude product was purified by preparative thin layer chromatography (silica gel, 2 mm) using 8:1:1 chloroform::methanol:toluene to yield 20 mg (37%) of rac-4'-(hydroxymethyl)-3',6'-dihydroxyspiro[isobenzofuran-1(3H),9'-[9H]xanthen]-3-one (2). NMR, IR and MS data confirmed the identity of the compound. To confirm the structural identity of compound (2), the compound was derivatized to the corresponding triacetate. NMR and MS data confirmed the identity of the triacetate. Hydrolysis of the triacetate yielded compound (2).

Example 2

Preparation of rac-4-(3',6'-dihydroxy-3-oxospiro [isobenzofuran-1(3H),9'-[9H]xanthen-4'-yl]methyl)-1-piperazinecarboxylic acid-1,1-dimethylethyl ester (3)

To a solution of 25 mg (0.065 mmol) of rac-4'-(hydroxymethyl)-3', 6'-dihydroxyspiro[isobenzofuran-1(3H),9'-[9H]xanthen]-3-one in 2 mL of anhydrous dimethylformamide was added 50 mg (0.26 mmol) of t-butyl piperazinecarboxylate followed by 100 µL (0.85 mmol) of 2,6 lutidine and 100 mg (0.66 mmol) of sodium iodide. The mixture was heated at 120° C. for 3 hours and then allowed to cool to room temperature. The reaction mixture was concentrated under reduced pressure. The residue was purified twice by preparative thin layer chromatography using 7:3 chloroform:methanol as the eluent to yield 10 mg (0.018 mmol, 30%) of rac-4-(3',6'-dihydroxy-3-oxospiro [isobenzofuran-1(3H),9'-[9H]xanthen-4'yl]methyl)-1- piperazinecarboxylic acid 1,1-dimethylethyl ester (3) as an orange-red powder. NMR, IR and MS data confirmed the compound identity.

Example 3

Preparation of rac-3',6'-dihydroxy-4'-(1-piperazinylmethyl spiro[isobenzofuran-1(3H),9'-[9H]xanthen]-3-one (4)

A mixture of 40 mg (0.75 mmol) of rac-4-(3',6'-dihydroxy-3-oxospiro[isobenzofuran-1(3H),9'-[9H] xanthen-4' yl]methyl)-1-piperazinecarboxylic acid 1,1-dimethylethyl ester (3) in 5 mL of trifluoroacetic acid was allowed to stir at room temperature for 15 minutes. The mixture was concentrated under reduced pressure. The residual trifluoroacetic acid was removed by codistillation with 3×5 mL of toluene. The remaining crude product was purified by thin layer chromatography using 1% triethylamine in methanol to yield 20 mg (0.46 mmol, 63%) of rac-3',6'-dihydroxy-4'-(1-piperazinylmethyl) spiro [isobenzofuran-1(3H),9'-[9H]xanthen]-3-one (4) as an orange solid. NMR, IR and MS data confirmed the compound identity.

Example 4

Preparation of tetrahydro-3-propylpyridin-2(1H)-one (6)

A solution of 4.2 g (42.3 mmol) of δ-valerolactam (5) in 35 mL of tetrahydrofuran was cooled to −78° C. under argon atmosphere. To this cooled solution, 32 mL of n-BuLi (2.5 M solution in hexane, 80 mmol) was added dropwise over a period of 40 minutes. The reaction mixture was warmed to room temperature and was magnetically stirred for 2 hours. The reaction mixture was cooled to 0° C. and a solution of 3.87 mL (42.5 mmol) of 1-bromopropane in 20 mL of tetrahydrofuran was added dropwise. The reaction mixture was warmed up to room temperature and stirred magnetically for 16 hours. The reaction mixture was treated with 75 mL of water and concentrated to remove tetrahydrofuran. The residue was extracted with 3×200 mL of diethyl ether. The organic layers were combined, washed with brine, dried over $MgSO_4$ and concentrated to yield a white solid which was recrystallized from petroleum ether to yield 3.2 g (22.6 mmol, 54%) of tetrahydro-3-propylpyridin-2(1H)-one (6). NMR, IR and MS data confirmed the compound identity.

Example 5

Preparation of rac-5-amino-2-propylpentanoic acid monohydrochloride (7)

A mixture of 2.0 g (14.1 mmol) of tetrahydro-3-propylpyridin-2(1H)-one (6) and 10 mL of 6N hydrochloric acid was heated to reflux for 6 hours, cooled to room temperature and concentrated under reduced pressure. The residue was codistilled with 2–50 mL of toluene to yield 1.9 g (11.9 mmol, 84%) of 5-amino-2-propylpentanoic acid monohydrochloride (7) as a pale yellow oil. NMR, IR and MS data confirmed compound identity.

Example 6

Preparation of rac-5-amino-2-propylpentanoic acid 1,1-dimethylethyl ester (8)

To a cooled solution of 7 mL of dioxane was added 0.7 mL of conc. $H_2SO_4$ dropwise. The solution turned purple in color. To this solution, 700 mg (3.5 mmol) of 5-amino-2-propylpentanoic acid monohydrochloride (7) was slowly added and the resulting solution was transferred into a pressure bottle. To this solution was added 12 mL of isobutylene and the resulting solution was slowly stirred magnetically under pressure at room temperature for 20 hours. The reaction vessel was cooled in dry ice, pressure was released, and the reaction vessel warmed up to room temperature to vaporize the excess isobutylene. The reaction mixture was poured into 100 mL of cold water. The aqueous part was extracted with 2×150 mL of ether, basified with 4N sodium hydroxide to pH 10, and extracted with 3×100 mL of ethyl acetate to yield 380 mg (1.76 mmol, 49%) of rac-5-amino-2-propylpentanoic acid 1,1-dimethylethyl ester (8) as an oil. NMR, IR and MS data confirmed the compound identity.

Example 7

Preparation of rac-5-[[(4-nitrophenoxy)carbonyl]amino]-2-propyl] pentanoic acid-1,1-dimethylethyl ester (9)

To a suspension of 160 mg (0.74 mmol) of rac-5-amino-2-propylpentanoic acid 1,1-dimethylethyl ester (8) in 1 mL of water and 1 mL of dichloromethane, 153 mg (0.76 mmol) of 4-nitrophenylchloroformate and 267 mg of sodium bicarbonate were added at 0° C. The mixture was stirred at room temperature overnight and then diluted with 50 mL of dichloromethane and 30 mL of water. The organic part was separated. The aqueous part was extracted with 2×50 mL of dichloromethane. The organic parts were combined and washed with 2×50 mL of 5% sodium bicarbonate followed by 50 mL of water, dried over MgSO$_4$ and concentrated. The residue was purified by preparative thin layer chromatography using 1:1 ethyl acetate:hexane as the eluent to yield 185 mg (0.48 mmol, 66%) of rac-5-[[(4-nitrophenoxy)carbonyl]amino]-2-propyl]pentanoic acid 1,1-dimethylethyl ester (9) asan offwhite solid. NMR, IR and MS data confirmed compound identity.

Example 8

Preparation of 5-[[[4-[(3',6'-dihydroxy-3-oxospiro[isobenzofuran-1(3H),9'-[9H]xanthen]-4'-yl)methyl]-1-piperazinyl]carbonyl]amino]-2-propylpentanoic acid 1,1-dimethylethyl ester (10)

To 20 mg (0.052 mmol) of (3) was added 1 mL of pyridine and 1 mL of dry dimethylformamide. To the resulting solution was added 26 mg (0.068 mmol) of rac-5-[[(4-nitrophenoxy)carbonyl]amino]-2-propyl] pentanoic acid 1,1-dimethylethyl ester (9). The resulting mixture was heated on a preheated oil-bath at 120° C. for 30 min. The reaction mixture was cooled to room temperature and concentrated under reduced pressure. The resulting residue was purified by preparative thin layer chromatography using 1:1 ethyl acetate:chloroform to yield 10 mg (0.014 mmol, 28%) of 5-[[[4-[(3',6'-dihydroxy-3-oxospiro[isobenzofuran-1(3H),9'-[9H] xanthen]-4'-yl)methyl]-1-piperazinyl]carbonyl]amino]-2-propylpentanoic acid 1,1-dimethylethyl ester (10). NMR, IR and MS data confirmed compound identity

Example 9

Preparation of 5-[[[4-[(3',6'-dihydroxy-3-oxospiro[isobenzofuran-1(3H),9'-[9H]xanthen]-4-yl)methyl]-1-piperazinyl]carbonyl]amino]-2-propylpentanoic acid (11)

To 15 mg (0.022 mmol) of 5-[[[4-[(3',6'-dihydroxy-3-oxospiro [isobenzofuran-1(3H),9'-[9H]xanthen]-4'-yl)methyl]-1-piperazinyl] carbonyl]amino]-2-propylpentanoic acid 1,1-dimethylethyl ester (10) was added 2 mL of trifluoroacetic acid. The mixture was allowed to stir at room temperature for 15 minutes. The resulting reaction mixture was concentrated and purified by thin layer column chromatography using 10:2 ethyl acetate:methanol as eluent to yield 8 mg (0.013 mmol, 61%) of 5-[[[4-[(3',6'-dihydroxy-3-oxospiro[isobenzofuran-1(3H),9'-[9H] xanthen]-4'-yl)methyl]-1-piperazinyl]carbonyl]amino]-2-propylpentanoic acid (11). NMR, IR and MS data confirmed compound identity.

Example 10

Preparation of rac-5-[[(3',6'-dihydroxy-3-oxospiro[isobenzofuran-1(3H),9'-[9H]xanthen]-6-yl)carbonyl] amino]-2-propylpentanoic acid (13)

A solution of 50 mg (0.13 mmol) 6-carboxyfluorescein in 1 mL of dimethylformamide was cooled to 0° C. To this was added 40 mg (0.19 mmol) of dicyclohexylcarbodiimide followed by 30 mg (0.26 mmol) of N-hydroxysuccinimide. The mixture was stirred at 4° C. for 24 hours and added dropwise to a solution of 50 mg (0.23 mmol) of (8) in 1 mL of pyridine and 0.3 mL of dry dimethylformamide. The reaction mixture was stirred at room temperature for 6 hours and concentrated. The residue was purified by preparative thin layer chromatography using 6:4 ethyl acetate:chloroform to yield 80 mg of rac-5-[[[3',6'-dihydroxy-3-oxospiro [isobenzofuran-1(3H),9'[9H]xanthen]-6-yl)carbonyl]amino]-2-propyl]-pentanoic acid 1,1-dimethylethyl ester (12). To 80 mg of (12) was added 3 mL of trifluoroacetic acid and the mixture was stirred at room temperature for 15 minutes. The reaction mixture was concentrated and purified by preparative thin layer chromatography (silica, 0.25 mm) to yield 42 mg (0.081 mmol, 62%) of rac-5-[[(3',6'-dihydroxy-3-oxospiro[isobenzofuran-1(3H),9'[9H]xanthen]-6-yl)carbonyl]amino]-2-propyl-pentanoic acid (13). NMR, IR and MS data confirmed the compound identity.

Example 11

Preparation of (S)-N-(1-methyl-2-phenylethyl) trifluoroacetamide (15)

A suspension of 10 g of d-amphetamine sulphate (14) in 55 mL of dichloromethane was treated with 54 mL of 1N sodium hydroxide. The organic layer was separated and the aqueous layer was extracted with 2×100 mL of dichloromethane. The pH of the aqueous layer was approximately 7.5 mL of 1N sodium hydroxide solution was added to the aqueous layer. The aqueous layer was then extracted with 2×50 mL of dichloromethane. All organic layers were combined and washed with 100 mL of brine, dried over MgSO$_4$ and concentrated to yield 6.6 g of amphetamine free base. To a solution of 6.6 g (48.8 mmol) of the amphetamine free base in 50 mL of distilled dichloromethane was added 40 mL of trifluoroacetic anhydride dropwise over a period of 1 hour under argon atmosphere at 0° C. The mixture was stirred at room temperature for 18 hours. To the reaction mixture was added 1 g of ice and 250 mL of ether. The organic layer was washed with 2×100 mL of water, 100 mL of saturated sodium acetate followed by 100 mL of water and dried over MgSO$_4$ to yield 8.35 g (36.7 mmol, 74%) of (S)-N-(1-methyl-2-phenylethyl) trifluoroacetamide (15). NMR, IR and MS data confirmed the compound identity.

Example 12

Preparation of (S)-4-[2-[(trifluoroacetyl)amino]propyl]benzenesulfonyl chloride(16)

To a solution of 2.0 g (8.64 mmol) of (S)-N-(1-methyl-2-phenylethyl)trifluoroacetamide (15) in 200 mL of chloroform was added 24 mL of chlorosulfonic acid dropwise at 0° C. The mixture was stirred at 0° C. for 4 hours. The reaction mixture was poured into 100 mL of ice water and extracted with 3×200 mL of chloroform. The organic layers were combined, dried over anhydrous sodium sulphate and evaporated to yield 2.58 g (7.82 mmol, 90%) of (S)-4-[2-[(trifluoroacetyl) amino]propyl]-benzenesulfonyl chloride (16) as a white solid. NMR, IR and MS data confirmed compound identity.

Example 13

Preparation of (S)-2,2,2-trifluoro-N-[1-methyl-2-[4-(1-piperazinylsulfonyl)phenyl]ethyl]acetamide (17)

To 856 mg (9.9 mmol) of piperazine was added 40 mL of freshly distilled tetrahydrofuran followed by 850 μL (6.09 mmol) of triethylamine. The mixture was stirred at room temperature. A solution of 830 mg (2.51 mmol) of (S)-4-[2-[(trifluoroacetyl)amino]propyl]benzene-sulfonyl chloride (16) in 25 mL of freshly distilled tetrahydrofuran was added dropwise to the above solution. The reaction mixture was stirred at room temperature for 18 hours and then was filtered. The filtrate was concentrated and redissolved in 200 mL of ethyl acetate, washed with 2×100 mL of water, dried over MgSO$_4$ and concentrated. The residue was purified by thin layer chromatography using 10% methanol in chloroform as the eluant to yield 780 mg (2.05 mmol, 82%) of (S)-2,2,2-trifluoro-N-[1-methyl-2-[4-(1-piperazinyl-sulfonyl)phenyl]ethyl]acetamide(17). NMR, IR and MS data confirmed compound identity.

Example 14

Preparation of (S)-N-[2-[4-[[4-[(3',6'-dihydroxy-3-oxospiro]isobenzo-furan-1(3H),9'-[9H]xanthen]-4'-yl)methyl]-1-piperazinyl]sulfonyl]-phenyl]-1-methylethyl]-2,2,2-trifluoroacetamide (18)

A mixture of 61 mg (0.160 mmol) of rac-4'-(hydroxymethyl)-3',6'-dihydroxyspiro[isobenzofuran-1 (3H), 9'-[9H]xanthen]-3-one (2), 125 mg (0.33 mmole) of (S)-2,2,2-trifluoro-N-[1-methyl-2-[4-(1-piperazinylsulfonyl)phenyl]ethyl]acetamide (17), 150 mg (1.0 mmol) of sodium iodide and 600 μL (5.15 mmol) of 2,6 lutidine in 4.5 mL of anhydrous dimethylformamide was heated at 120° C. for 2 hours. The reaction mixture was concentrated and 20 mL of a 1:1 mixture of methanol:THF was added. Inorganic salt was filtered off and the filtrate was concentrated. The residue was purified by thin layer chromatography using 50% chloroform in ethyl acetate to yield 41 mg of (S)-N-[2-[4-[[4-[(3',6'-dihydroxy-3-oxospiro[isobenzo-furan-1(3H),9'-[9H]xanthen]-4'-yl)methyl]-1-piperazinyl]-sulfonyl]phenyl]-1-methylethyl]-2,2,2-trifluoroacetamide (1:1 epimers) (18) (0.056 mmol, 35%) as an orange red powder. NMR, IR and MS data confirmed the compound identity.

Example 15

Preparation of (S)-4'-[[4-(2-aminopropyl)phenyl] sulfonyl]-1-piperazinyl]methyl]-3',6'-dihydroxyspiro [isobenzofuran-1(3H)-9'-[9H]xanthen]-3-one (19)

To 31 mg (0.042 mmol) of (S)-N-[2-[4-[[4-[(3',6'-dihydroxy-3-oxospiro[isobenzofuran-1(3H),9'-[9H] xanthen]-4'-yl)methyl]-1-piperazinyl]-sulfonyl]phenyl]-1-methylethyl]-2,2,2-trifluoroacetamide (18) was added 2 mL of methanol followed by 2 mL of saturated methyl amine in methanol. The mixture was heated at 60° C. for 24 hours and concentrated. The residue was purified by thin layer chromatography using 8:2 chloroform:methanol to yield 10 mg (0.015 mmol, 38%) of (S)-4'-[[4-(2-aminopropyl)phenyl] sulfonyl]-1-piperazinyl]methyl]-3',6'-dihydroxyspiro-[isobenzofuran-1(3H)-9'-[9H]xanthen]-3-one (1:1 epimers) (19) as an orange red powder. NMR, IR and MS data confirmed compound identity.

Example 16

Preparation of 1-[(2-methoxyethoxy)methoxy]-4-nitrobenzene (21)

To 200 mg (0.5 mmol) of sodium hydride (60% dispersion in oil) was added 10 mL of hexane. After settling, the hexane was decanted. To the residue was added 10 mL of freshly distilled tetrahydrofuran and the slurry mixture was cooled at 0° C. To this was added slowly 200 mg (1.43 mmole) of 4-nitrophenol (20) as a solid portionwise. The reaction mixture was stirred at 0° C. for 5 minutes and 197 μL (1.71 mmol) of 2-methoxyethoxy methyl chloride was added. The mixture was stirred at room temperature for 18 hours. To the reaction mixture 25 mL of water was slowly added and the reaction mixture was diluted with 50 mL of ethyl acetate. The organic part was separated and the aqueous layer was extracted with 2×50 mL of ethyl acetate. The organic layers were combined and washed with 7×100 mL of saturated sodium carbonate solution, followed by 100 mL of water. The ethyl acetate layer was dried over MgSO$_4$ and concentrated to yield 225 mg (0.99 mmol, 69%) of 1-[(2-methoxyethoxy)methoxy]-4-nitrobenzene (21) as a pale yellow oil. NMR, IR and MS data confirmed compound identity.

Example 17

Preparation of 4-[(2-methoxyethoxy)methoxy] benzenamine(22)

A mixture of 200 mg (0.88 mmol) of 1-[(2-methoxyethoxy) methoxy]-4-nitrobenzene (21), 100 mg of 10% Pd/C and 550 mg (8.7 mmol) of ammonium formate in 10 mL of absolute ethanol was stirred at room temperature for 18 hours. The reaction mixture was diluted with 100 mL of absolute ethanol and passed through a small pad of celite. The filtrate was concentrated and purified by silica gel column chromatography using 8:2 ethyl acetate:hexane as the eluent to yield 130 mg (0.65 mmol, 75%) of 4-[(2-methoxyethoxy)methoxy]benzenamine (22). NMR, IR and MS data confirmed compound identity.

Example 18

Preparation of 4-[[4-[(2-methoxyethoxy)methoxy] phenyl]amino]-4-oxobutanoic acid (23)

To a solution of 510 mg (2.58 mmol) of 4-[(2-methoxyethoxy) methoxy]benzenamine (22) in 8 mL of dichloromethane and 2 mL of anhydrous pyridine (Aldrich) was added 380 mg (3.8 mmol) of succinic anhydride portionwise. The mixture was stirred at room temperature for 18 hours. To the reaction mixture was added 20 mL of methanol and the mixture was stirred at room temperature for 2 hours. The mixture was concentrated and purified by preparative thin layer chromatography using 8:2 chloroform:methanol as an eluent to yield 420 mg (1.41 mmol, 55%) of 4-[[4-[(2-methoxyethoxy)methoxy]phenyl]amino]-4-oxobutanoic acid (23). NMR, IR and MS data confirmed the compound identity.

Example 19

Preparation of N-[4-[(2-methoxyethoxy)methoxy]phenyl]-gamma-oxo-1-piperazinebutamide(24)

To a solution of 407 mg (1.36 mmol) of 4-[[4-[(2-methoxyethoxy) methoxy]phenyl]amino]-4-oxobutanoic acid (23) in 8 mL of anhydrous dimethylformamide (Aldrich) was added 339 mg (1.64 mmol) of dicyclohexylcarbodiimide and 236 mg (2.05 mmol) of N-hydroxysuccinimide at 0° C. The mixture was stirred at 4° C. for 18 hours. The active ester was used in situ without isolation in the following reaction. To a solution of 1.4 g (16.2 mmol) of piperazine in 20 mL of freshly distilled tetrahydrofuran was added 1.5 mL of triethylamine. To this mixture was added the previously prepared N-hydroxysuccinimide ester solution dropwise at room temperature and the mixture was stirred magnetically at room temperature for 2 days. The reaction mixture was concentrated. The residue was purified by silica gel column chromatography using 6:4 ethyl acetate:methanol to yield 384 mg (1.05 mmol, 77%) of N-[4-[(2-methoxyethoxy)methoxy]phenyl]gammaoxo-1-piperazinebutamide (24). NMR, IR and MS data confirmed compound identity.

Example 20

Preparation of rac-4-[(3',6'-dihydroxy-3-oxospiro[isobenzofuran-1(3H),9'-[9H]xanthen]-4'-yl)methyl]-N-(4-hydroxyphenyl)-gamma-oxo-1-piperazinebutamide (26)

To a mixture of 30 mg (0.082 mmol) of N-[4-[(2-methoxy ethoxy)methoxy]phenyl]-gamma-oxo-1-piperazine butamide (24) and 35 mg (0.091 mmol) of rac-4'-(hydroxymethyl)-3',6'-dihydroxyspiro[isobenzofuran-1(3H) 9'-[9H]xanthen]-3-one (2) in 2.5 mL of dimethylformamide was added 250 μL (2.14 mmol) of 2,6-lutidine and 100 mg (0.66 mmol) of sodium iodide. The mixture was heated at 140° C. for 3 hours under argon atmosphere. The reaction was monitored by thin layer chromatography using 9:1 chloroform:methanol as the eluent which indicated the presence of the new product as well as a significant amount of N-[4-[(2-methoxyethoxy)methoxy]phenyl]-gamma-oxo-1-piperazinebutamide (24). To the reaction mixture was additionally added 25 mg (0.065 mmol) of compound (2) and the mixture was heated for another 2.5 hours. The reaction mixture was concentrated and purified twice by preparative thin layer chromatography to yield 15 mg (0.021 mmol, 26%) of rac-4-[3',6'-dihydroxy-3-oxospiro[isobenzofuran-1(3H),9'[9H]xanthen]-4'-yl)methyl]-N-[(4-[2-methoxyethoxy)methoxy]phenyl]-gamma-oxo-1-piperazinebutamide (25). To 15 mg (0.021 mmol) of (25) was added 3 mL of trifluoroacetic acid and the mixture was stirred at room temperature for 30 minutes. The resulting reaction mixture was concentrated and purified by thin layer chromatography using 9:1 chloroform:methanol as the eluent to yield 7mg (0.011 mmol, 54%) of rac-4-[(3',6'-dihydroxy-3-oxospiro[isobenzofuran-1(3H),9'-[9H]xanthen]-4'-yl)methyl]-N-(4-hydroxyphenyl)-gamma-oxo-1-piperazinebutamide (26). NMR, IR and MS data confirmed the compound identity.

Example 21

Preparation of rac-4-[[[3',6'-dihydroxy-3-oxospiro[isobenzofuran-1(3H),9'-[9H]xanthen]-4'-yl)methyl]amino]-N-(4-hydroxyphenyl)-4-oxobutamide(28)

To a solution of 120 mg (0.40 mmol) of 4-[[4-[(2-methoxyethoxy) methoxy]phenyl]amino-4-oxobutanoic acid (23) in 2.5 mL of anhydrous dimethylformamide was added 83 mg (0.40 mmol) of dicyclohexylcarbodiimide and 60 mg (0.52 mmol) of N-hydroxysuccinimide at 0° C. under argon atmosphere. The resulting mixture was stirred at 4° C. for 24 hours. The N-hydroxysuccinimide ester generated in situ was added dropwise under argon atmosphere to a magnetically stirred solution of 25 mg (0.062 mmol) of 4'-aminomethylfluorescein hydrochloride in 2 mL of dry pyridine. The resulting mixture was stirred at room temperature for 48 hours and concentrated under reduced pressure to yield 15 mg of (0.023 mmol, 38%) of rac-4-[3',6'-dihydroxy-3-oxospiro[isobenzofuran-1(3H),9'[9H]xanthen]-4-yl)methyl]amino]-N-[(4-[(2-methoxyethoxy)methyl]phenyl]-4-oxobutamide (27) as an orange residue. To 15 mg (0.023 mmol) of (27) was added 3 mL of trifluoroacetic acid and the mixture was stirred at room temperature for 30 minutes. The reaction mixture was concentrated and purified by thin layer chromatography using 8:2 chloroform:methanol to yield 8 mg (0.014 mmol, 67%) of rac-4'-[[[3',6'-dihydroxy-3-oxospiro[isobenzofuran-1(3H),9'-[9H]xanthen]-4'-yl)methyl] amino]-N-(4-hydroxyphenyl)-4-oxobutamide (28) as an orange powder. NMR, IR and MS data confirmed compound identity.

Example 22

Preparation of (S)-4-[(4-hydroxy-3,5-diiodo)-phenoxy-3,5-diiodo]-α[[(1,1-dimethylethoxy)carbonyl]amino]benzenepropanoic acid (30).

To a magnetically stirred mixture of 4.5 g (5.8 mmol) of L-thyroxine (29) in 18 mL of dimethylformamide, 495 mg (5.9 mmol) of sodium bicarbonate and 18 mL of water was added dropwise a solution of 1.28 g (5.8 mmol) of di-t-butyl dicarbonate in 18 mL of dimethylformamide. The resulting reaction mixture was stirred for 4 hours, then concentrated under high vacuum at room temperature. To the residue, 45 mL of methanol was added, and the undissolved material was filtered off. To the filtrate 1N hydrochloric acid solution (20 mL) was added until the precipitation was complete. The solid was filtered off and air dried to yield 4.2 g (4.8 mmol, 83%) of (S)-4-[(4-hydroxy-3,5-diiodo)phenoxy-3,5-diiodo]-α-[[(1,1-dimethylethoxy)carbonyl]amino] benzenepropanoic acid (30) as an off-white powder. NMR, IR and MS data confirmed the compound identity.

Example 23

Preparation of (S)-[1-[(hexahydro-1H-1,4-diazepin-1-yl)carbonyl]-2-[4-[(4-hydroxy-3,5-diiodo)phenoxy]-3,5-diiodophenyl]ethyl]carbamic acid 1,1-dimethylethyl ester (31)

A magnetically stirred solution of 1.8 g (2.05 mmole) of (S)-4-[(4-hydroxy-3,5-diiodo)phenoxy-3,5-diiodophenyl]-α-[[(1,1dimethylethoxy)-carbonyl]amino] benzenepropanoic acid (30) in 55 mL of dry dimethylformamide (Aldrich sure seal, 99%) was charged with 539 mg (4.68 mmol) of N-hydroxysuccinimide followed by 1.02 g (5.32 mmol) of 1-ethyl-3-(3-dimethylaminopropyl) carbodiimide. The mixture was stirred at room temperature for 2.5 hours, and then was added dropwise to a solution of 3.6 g (36 mmol) of homopiperazine in 20 mL of dry pyridine over a period of 25 minutes. The resulting reaction mixture was stirred at room temperature overnight and concentrated under high vaccum. To the resulting gummy residue was added 250 mL of saturated sodium bicarbonate solution. The mixture was filtered to yield 2.5 g of off-white solid crude product. The solid was purified by flash column chromatography using 1:1 methanol:chloroform to provide 1.3 g (1.35 mmol, 66%) of (S)-[1-[(hexahydro-1H-1,4-diazepin-1-yl) carbonyl]-2-[4-[(4-hydroxy-3,5-diiodo)phenoxy]-3,5-diiodophenyl]ethyl]carbamic acid-1,1-dimethylethyl ester (31) as an off-white solid. NMR, IR and MS data confirmed compound identity.

Example 24

Preparation of (2S)-4'-[[4-[2-amino-3-[4-(4-hydroxy-3,5-diiodophenoxy)-3,5-diiodophenyl]-1-oxopropyl]-1-piperazinyl]methyl]-3',6'-dihydroxyspiro[isobenzofuran-1(3H)9'-[9H] xanthen]-3-one (1:1 epimer) (33)

To a solution of 126 mg (0.131 mmol) of (S)-[1-[(hexahydro-1H-1,4-diazepin-1-yl)carbonyl]-2-[4-[(4-hydroxy-3,5-diiodo)phenoxy]-3,5-diiodophenyl]ethyl] carbamic acid 1,1-dimethylethyl ester (31) in 2 mL of anhydrous dimethylformamide was added 400 μl (3.4 mmol) of 2,6-lutidine, 200 mg (1.3 mmol) of sodium iodide followed by 50 mg (131 mmol) of rac-4'-(hydroxymethyl)-3', 6'-dihydroxyspiro[isobenzofuran-1(3H),9'-[9H]xanthen]-3-one (2). The mixture was heated to 130° C. for 3 hours and concentrated under reduced pressure to yield 52 mg (0.048 mmol, 37%) of (2S)-4'-[4'-[[4-[2[(1,1-dimethylethoxy) carbonyl]amino-3-[4-(4-hydroxy-3,5-diiodophenoxy)-3,5-diiodophenyl]-1-oxopropyl]-1-piperazinyl]methyl]-3',6'-dihydroxyspiro[isobenzofuran-1(3H)9'-[9H]xanthen]-3-one (32) as a residue. To 52 mg (0.048 mmol) of (32) was added 3 mL of trifluoroacetic acid. The mixture was stirred at room temperature for 5 minutes and concentrated. The residue was purified twice by preparative thin layer chromatography using 8:2 chloroform:methanol to yield 15 mg (0.011 mmol, 24%) of (2S)-4'-[4'-[2-amino-3-[4-(4-hydroxy-3,5-diiodophenoxy)-3,5-diiodophenyl]-1-oxopropyl]-1-piperazinyl]methyl]-3',6'-dihydroxyspiro[isobenzofuran-1 (3H)9'-[9H]xanthen]-3-one (1:1 epimers) (33) as an orange powder. NMR, IR and MS data confirmed the compound identity.

Example 25

Preparation of 5H-dibenz[b,f]azepine-5-carbonylchloride (35)

A solution of 2.8 g of iminostilbene (34) in 100 mL of dichloromethane was treated with 1.5 g of triphosgene followed by 3 mL of pyridine and stirred at room temperature overnight. Thin layer chromatography in 40% ethyl acetate-hexane indicated formation of one product. The reaction mixture was washed with water and concentrated in vaccuo. The residue was chromatographed on silica using 10% ether/dichloromethane to yield 3.2 g of 5H-dibenz[b, f]azepine-5-carbonylchloride (35) as an off-white powder. NMR, IR and MS data confirmed the compound identity.

Example 26

Preparation of N-(4-piperidinylmethyl)-5H-dibenzo [b,f]azepine-5-carboxamide (36)

To a solution of 511 mg (2 mmol) of 5H-dibenzo[b,f] azepine-5-carbonylchloride (35) in 15 mL of anhydrous dimethylformamide was added 280 μL of triethylamine followed by 2.3 g (2.0 mmol) of 4-aminomethylpiperidine. The mixture was stirred at room temperature overnight and concentrated under reduced pressure. To the residue was added 200 mL of dichloromethane and 150 mL of saturated sodium bicarbonate solution. The organic layer was separated and the aqueous layer was extracted with 2×100 mL of dichloromethane. The organic layers were combined and dried over $MgSO_4$ to yield a crude product which was purified by thin layer chromatography using 9.5:0.5 methanol:conc. ammonium hydroxide to yield two isomeric products. The slower running component was isolated and yielded 350 mg (1.04 mmol, 53%) of N-(4-piperidinylmethyl)-5H-dibenzo[b,f]azepine-5-carboxamide (36) as an off-white solid. NMR and MS data confirmed compound identity.

Example 27

Preparation of N-[[1-[(3',6'-dihydroxy-3-oxospiro [isobenzofuran-1(3H)-9'-[9H]-xanthen]-4'-yl) methyl]-4-piperidinyl]methyl]-5H-dibenzo[b,f] azepine-5-carboxamide (37)

To a solution of 35 mg (0.104 mmol) of N-(4-piperidinylmethyl)-5H-dibenzo[b,f]azepine-5-carboxamide (36) in 3 mL of anhydrous dimethylformamide was added 200 μL (1.71 mmol) of 2,6 lutidine, 200 mg (1.3 mmol) of sodium iodide followed by 40 mg (0.105 mmol) of rac-4'-(hydroxymethyl)- 3',6'-dihydroxyspiro[isobenzofuran-1 (3H),9'-[9H] xanthen]-3-one (2). The mixture was stirred at 140° C. for 3 hours under argon atmosphere and concentrated under reduced pressure. The residue was purified by thin layer chromatography using 7:3:1 ethyl acetate:chloroform:methanol as the eluent to yield an orange product which contained impurities. This was repurified by thin layer chromatography using 8:2 chloroform:methanol as the eluent to yield 15 mg ( 0.022 mmol, 21%) of N-[[1-[(3',6'-dihydroxy-3-oxospiro[isobenzofuran-1(3H)-9'-[9H]-xanthen]-4'-yl)methyl]-4-piperidinyl]methyl]-5H-dibenzo [b,f]azepine-5-carboxamide (37) as an orange powder. NMR, IR and MS data confirmed compound identity.

Example 28

Preparation of N-bromoacetyliminostilbene (38)

A solution of 6.0 g (0.03 mole) of iminostilbene in 250 mL of chloroform was added to a solution of 10 g (0.09 mole) of sodium carbonate in 100 mL of water and the mixture was stirred rapidly. To this rapidly stirring solution 6.2 g (0.03 mole) of bromoacetyl bromide was added dropwise through an additional funnel, at which time thin layer chromatography analysis using 2:1 THF:hexane indicated the reaction was incomplete. An additional 1.0 g (0.005 mole) of bromoacetyl bromide was added. Thin layer chromatography indicated that the starting material had been totally consumed. The chloroform layer was separated, dried over $Na_2SO_4$ and concentrated to yield 11.0 g of N-bromoacetyliminostilbene (38) as a light yellow oil. This material was used in the following reaction.

Example 29

Preparation of 5-(aminoacetyl)-5H-dibenzo[b,f] azepinehydrochloride(39)

A solution of 2.2 g (7 mmol) of crude N-bromoacetyliminostilbene (38) in 25 mL of chloroform was added carefully to 250 mL of condensed liquid ammonia at −33° C. To the reaction mixture 6.0 g (40 mmol) of sodium iodide was added, the mixture was stirred at −33° C. for 2 hours and evaporated overnight. A water-white oily solution remained and 50 mL of water was added. The solution was extracted with 2×150 mL of chloroform. The solvent was dried over $Na_2SO_4$ and evaporated to yield a clear oil that was dissolved in 25 mL of methanol saturated with hydrochloric acid (g). The resulting solution was concentrated and 25 mL of acetonitrile was added. The solid material precipitated was collected and washed with 10 mL of acetonitrile. Recrystallization in methanol/ether gave 1.8 g (6.2 mmol, 90%) of 5-(aminoacetyl)-5H-dibenzo[b,f] azepinehydrochloride (39). NMR, IR and MS data confirmed compound identity.

Example 30

Preparation of N-[(5H-dibenz[b,f]azepin-5-ylcarbonyl)methyl]-N'-3',6'-dihydroxy-3-oxospiro [isobenzofuran-1(3H),9'-[9H]xanthen-5-yl] thiourea dihydrate (40)

A solution of 1.0 g (4 mmol) of 5-(aminoacetyl)-5H-dibenzo[b,f] azepinehydrochloride (39) in a mixture of 75 mL of dry methanol and 75 mL of dry tetrahydrofuran was treated with 1.4 g (3.6 mmol) of 5-fluorescein isothiocyanate (isomer I) and stirred at room temperature overnight. The solvent was removed under reduced pressure and the residue was purified by column chromatography using 12% methanol in chloroform as the eluent to yield 800 mg (1.18 mmol, 35%) of N-[(5H-dibenzo[bf] azepin-5-ylcarbonyl)methyl]-N'-3',6'-dihydroxy-3-oxospiro [isobenzofuran-1(3H),9'-[9H]xanthen-5-yl]thiourea dihydrate (40) as a red solid. NMR, IR and MS data confirmed compound identity.

Example 31

Fluorescence Polarization Immunoassay using the novel 4'-methyl fluorescein tracers of the present invention The performance of the novel compounds of the present invention was measured on the automated COBAS FARA® II (Roche Diagnostic Systems Inc., Branchburg, N.J.) using assay reagents and protocols in accordance with the operation manual for the instrument.

By way of example, the instrument was configured for fluorescence polarization measurements for acetaminophen in serum or plasma samples
I) Reagent Formulations:
  a) Antibody Reagent
    0.1M Phosphate buffer pH 7.5 containing 0.1% sodium azide and 0.1% bovine gamma globulin;
    antibody diluted in a range from 1:5 to 1:40.
  b) Tracer Reagent
    0.1M phosphate buffer pH 7.5 containing 0.1% bovine gamma globulin and 0.1% sodium azide;
    $5×10^{-7}$ M tracer.
  c) Acetaminophen Calibrators:
    Solutions of 0, 10, 20, 50, 100 and 200 μg/mL acetaminophen in normal human serum.

For each sample of acetaminophen tracer described in the examples above:
1) 200 μL of antibody reagent was mixed with 30 μL of a calibrator solution;
2) a background polarization reading was taken;
3) 5.2 μL of tracer reagent was added;
4) the mixture was incubated for 30 seconds;
5) a polarization reading was taken; and
6) the span of the tracer was calculated.

We claim:
1. A compound of the formula

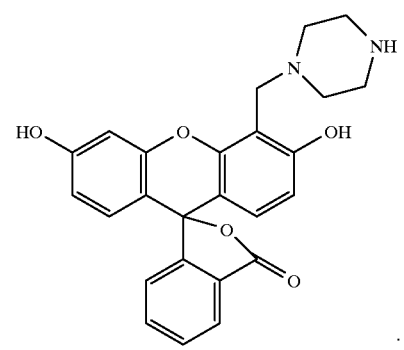

4

2. A compound of the formula

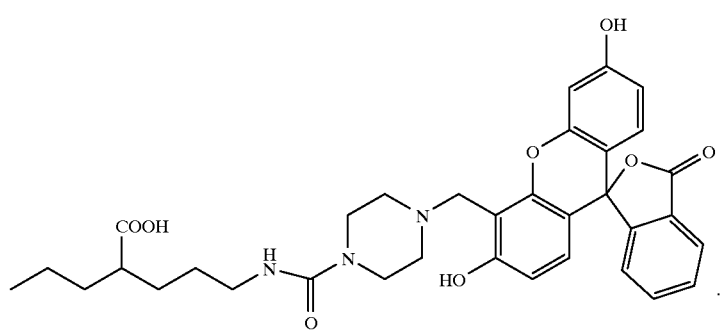

11

* * * * *